(12) United States Patent
Chen et al.

(10) Patent No.: US 10,265,854 B2
(45) Date of Patent: Apr. 23, 2019

(54) OPERATING ROOM SAFETY ZONE

(71) Applicants: Synaptive Medical (Barbados) Inc., Bridgetown (BB); Sean Jy-Shyang Chen, Toronto (CA); Kirusha Srimohanarajah, Toronto (CA); Gal Sela, Toronto (CA); Joshua Richmond, Toronto (CA); Kelly Dyer, Toronto (CA)

(72) Inventors: Sean Jy-Shyang Chen, Toronto (CA); Kirusha Srimohanarajah, Toronto (CA); Gal Sela, Toronto (CA); Joshua Richmond, Toronto (CA); Kelly Dyer, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 89 days.

(21) Appl. No.: 15/228,853

(22) Filed: Aug. 4, 2016

(65) Prior Publication Data
US 2018/0036884 A1 Feb. 8, 2018

(51) Int. Cl.
*B25J 9/16* (2006.01)
*A61B 34/30* (2016.01)
(Continued)

(52) U.S. Cl.
CPC ............. *B25J 9/1676* (2013.01); *A61B 34/20* (2016.02); *A61B 34/30* (2016.02); *A61B 90/03* (2016.02);
(Continued)

(58) Field of Classification Search
CPC ...... B25J 9/1666; B25J 9/1976; B25J 9/1692; G05B 2219/40476; A61B 34/30; A61B 34/20
See application file for complete search history.

(56) References Cited

U.S. PATENT DOCUMENTS

| 2004/0024311 | A1* | 2/2004 | Quaid, III | A61B 90/36 600/428 |
| 2004/0106916 | A1* | 6/2004 | Quaid | A61B 34/71 606/1 |

(Continued)

FOREIGN PATENT DOCUMENTS

WO 2014139023 9/2014

OTHER PUBLICATIONS

A Wytyczak-Partyk et al, "Safety Oriented Laparoscopic Surgery Training System".

(Continued)

*Primary Examiner* — Dale Moyer
(74) *Attorney, Agent, or Firm* — Ridout & Maybee LLP

(57) ABSTRACT

Methods and devices for identifying and defining a safety zone for restricting movement of a robotic arm in an operating room during a medical procedure are disclosed. The disclosed method utilizes medical navigation system, which receives an initiation input indicating initiation of defining of the safety zone. In response to receiving the initiation input, the system tracks an instrument and determines the location of the tracked instrument relative to a reference point. The system detects changes in the location of the tracked instrument until a termination input is received at the medical navigation system. The termination input indicates the termination of the defining of the safety zone. The system stores, in memory, change data indicative of the changes in the location of the tracked instrument. The data identifies the safety zone relative to the reference point.

20 Claims, 16 Drawing Sheets

(51) Int. Cl.
*A61B 34/20* (2016.01)
*A61B 90/00* (2016.01)

(52) U.S. Cl.
CPC ............... *A61B 2034/2055* (2016.02); *G05B 2219/36541* (2013.01); *Y10S 901/02* (2013.01)

(56) References Cited

U.S. PATENT DOCUMENTS

| | | | |
|---|---|---|---|
| 2014/0180290 A1* | 6/2014 | Otto | A61B 17/1703 606/80 |
| 2014/0222023 A1 | 8/2014 | Kim et al. | |
| 2014/0276943 A1* | 9/2014 | Bowling | A61B 19/2203 606/130 |

OTHER PUBLICATIONS

Rosario Feghali and Amar Mitiche, "Spatiotemporal Motion Boundary Detection and Motion Boundary Velocity Estimation for Tracking Moving Objects With a Moving Camera: A Level Sets PDEs Approach With Concurrent Camera Motion Compensation", IEEE Transactions on Image Processing, vol. 13, No. 11, Nov. 2004.
Stephen C. Schimpff, "The Future of Medicine: Megatrends in Health Care That Will Improve Your Quality of Life" (Book).

* cited by examiner

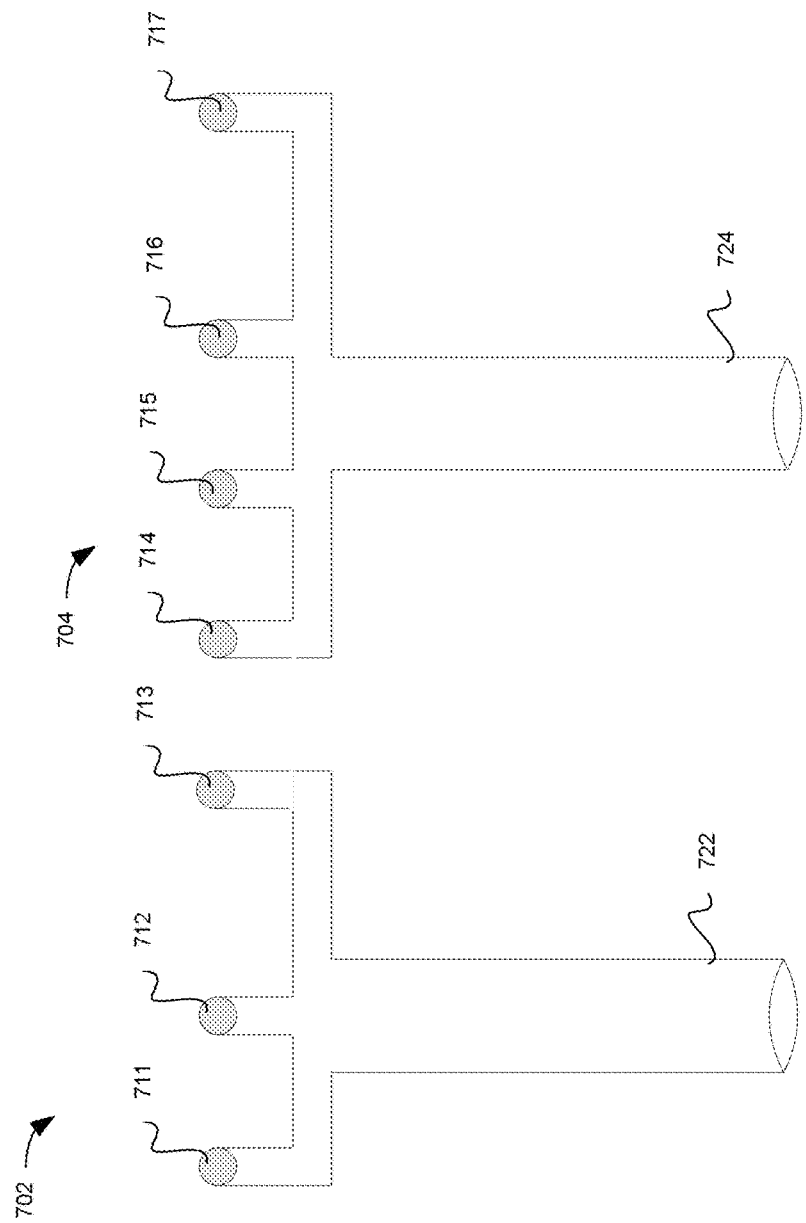

OPERATING ROOM SAFETY ZONE

TECHNICAL FIELD

The present disclosure generally relates to defining a safety zone in an operating room configured for image guided medical procedures, the safety zone restricting movement of a robotic arm.

BACKGROUND

In the example of a port-based surgery, a surgeon or robotic surgical system may perform a surgical procedure involving tumor resection in which the residual tumor remaining after is minimized, while also minimizing the trauma to the intact white and grey matter of the brain. In such procedures, trauma may occur, for example, due to contact with the access port, stress to the brain matter, unintentional impact with surgical devices, and/or accidental resection of healthy tissue.

Referring to FIG. 1, this diagram illustrates the insertion of an access port into a human brain, for providing access to internal brain tissue during a medical procedure, in accordance with the related art. The access port 12 is inserted into a human brain 10, providing access to internal brain tissue, wherein the access port 12 may include such instruments as catheters, surgical probes, or cylindrical ports, such as the NICO® BrainPath®. Surgical tools and instruments may then be inserted within the lumen of the access port in order to perform surgical, diagnostic, or therapeutic procedures, such as resection of tumors, as necessary.

Still referring to FIG. 1, access port surgery may be utilized in conjunction with catheters, deep brain stimulation ('DBS') needles, a biopsy procedure, and also to biopsies and/or catheters in other medical procedures performed on other parts of the body. In the example of a port-based surgery, a straight or linear access port 12 is typically guided down a sulci path of the brain. Surgical instruments would then be inserted down the access port 12. Optical tracking systems may be used with such medical procedures for tracking the position of a part of the instrument that is within line-of-site of the optical tracking camera. These optical tracking systems also require a reference to the patient to know where the instrument is relative to the target (e.g., a tumour) of the medical procedure.

In the field of medicine, imaging and image guidance are a significant component of clinical care. From diagnosis and monitoring of disease, to planning of the surgical approach, to guidance during procedures and follow-up after the procedure is complete, imaging and image guidance provides effective and multifaceted treatment approaches, for a variety of procedures, including surgery and radiation therapy. Targeted stem cell delivery, adaptive chemotherapy regimes, and radiation therapy are only a few examples of procedures utilizing imaging guidance in the medical field.

Advanced imaging modalities such as Magnetic Resonance Imaging ("MRI") have led to improved rates and accuracy of detection, diagnosis and staging in several fields of medicine including neurology, where imaging of diseases such as brain cancer, stroke, Intra-Cerebral Hemorrhage, and neurodegenerative diseases, such as Parkinson's and Alzheimer's, are performed. As an imaging modality, MRI enables three-dimensional visualization of tissue with high contrast in soft tissue without the use of ionizing radiation. This modality is often used in conjunction with other modalities such as Ultrasound ("US"), Positron Emission Tomography ("PET") and Computed X-ray Tomography ("CT"), by examining the same tissue using the different physical principals available with each modality. CT is often used to visualize boney structures and blood vessels when used in conjunction with an intra-venous agent such as an iodinated contrast agent. MRI may also be performed using a similar contrast agent, such as an intra-venous gadolinium-based contrast agent having pharmaco-kinetic properties that enable visualization of tumors and break-down of the blood brain barrier.

In neurosurgery, for example, brain tumors are typically excised through an open craniotomy approach guided by imaging. The data collected in these solutions typically consists of CT scans with an associated contrast agent, such as iodinated contrast agent, as well as MRI scans with an associated contrast agent, such as gadolinium contrast agent. Also, optical imaging is often used in the form of a microscope to differentiate the boundaries of the tumor from healthy tissue, known as the peripheral zone. Tracking of instruments relative to the patient and the associated imaging data is also often achieved by way of external hardware systems such as mechanical arms, or radiofrequency or optical tracking devices. As a set, these devices are commonly referred to as surgical navigation systems.

Three dimensional (3-D) sensor systems are increasingly being used in a wide array of applications, including medical procedures. These sensor systems determine the shape and/or features of an object positioned in a scene of the sensor system's view. In recent years, many methods have been proposed for implementing 3-D modeling systems that are capable of acquiring fast and accurate high resolution 3-D images of objects for various applications.

Triangulation based 3-D sensor systems and methods typically have one or more projectors as a light source for projecting onto a surface and one or more cameras at a defined, typically rectified relative position from the projector for imaging the lighted surface. The camera and the projector therefore have different optical paths, and the distance between them is referred to as the baseline. Through knowledge of the baseline distance as well as projection and imaging angles, known geometric/triangulation equations are utilized to determine distance to the imaged object. The main differences among the various triangulation methods known in the related art lie in the method of projection as well as the type of light projected, typically structured light, and in the process of image decoding to obtain three dimensional data.

A 3-D sensor system may be contemplated as a novel extension of a surgical navigation systems. One popular triangulation based 3-D sensor system is created by Mantis Vision®, which utilizes a single frame structured light active triangulation system to project infrared light patterns onto an environment. Other systems include Creaform 3D™ and Intel® RealSense™. To capture 3-D information, a projector overlays an infrared light pattern onto the scanning target. In an alternative system, Fuel3D Scanify®, the projector overlays visible light from multiple light sources. Thereafter, a digital camera and a depth sensor, synchronized with the projector, capture the scene with the light reflected by the object for at least the timeframe of one frame of the 3-D scan. This technique is applicable even in complete darkness, since the digital camera includes its own illumination; and, in bright environments, the quality of the resulting image depends on the hardware used.

During a related art medical procedure, navigation systems require a registration to transform between the physical position of the patient in the operating room and the volumetric image set, e.g., MRI/CT. Conventionally, this registration is done to the position of a reference tool, which is visible by the tracking system and stays fixed in position and orientation relative to the patient throughout the procedure. This registration is typically accomplished through correspondence touch points, e.g., either fiducial or anatomic points. Such an approach to registration has a number of disadvantages, including requiring fiducials to be placed before scans, requiring points to be identified, providing for a limited number of points, touch point collection is subject to user variability, and the physical stylus used for collecting the points can deform or deflect patient skin position.

Another conventional approach to collecting the touch points in the related art includes performing a surface tracing of the patient drawn as a line which is matched to the image set surface contour using either a stylus pointer or a laser pointer. Such an approach to registration has a number of disadvantages, including providing for a limited number of points, and the physical stylus can deform or deflect patient skin position. Yet another conventional approach to collecting the touch points includes using a mask, which requires a high level of operator training and is operator dependent. This approach also provides only a limited number of points.

Other common limitations of the foregoing conventional approaches to registration include a that a stylus needs to remain visible to the tracking system, which may not necessarily be possible depending on a patient's surgical position or may introduce surgical restrictions that need to be accounted in planning, and error accumulation where touch point or tracing collection is of low quality resulting in error propagation through subsequent steps of the registration. Further, using the conventional methods, if registration is lost, re-registration is difficult to be completed again during the surgical procedure.

In the related art, surgery, such as neurosurgery, for example, brain tumors are typically excised through an open craniotomy approach guided by imaging. Optical imaging is often used in the form of a microscope to differentiate the boundaries of the tumor from healthy tissue, known as the peripheral zone. Tracking of instruments relative to the patient and the associated imaging data is also often achieved by way of external hardware systems such as mechanical arms, radiofrequency, or optical tracking devices.

Some related art tracking systems use tracking markers disposed on a surgical instrument for facilitating navigation of such surgical instrument during surgery. Other related art tracking systems involve using tracking markers on a patient that are detectable during scanning or imaging. In such related art tracking systems, prior to treatment, a retroreflective, apertured, disk is applied to the patient precisely at a location defined by a "tattoo" wherein an aperture or hole is at a center of the disk is used to register the disk with the tattoo. The retroreflective, apertured, disk is detectable by a camera. In a related art tracking system, RFID tags are used on or in bandages for verifying or counting various items.

Other related art tracking solutions, such as Servo®, do not track the position and gaze of the surgeon during a surgical procedure. As a result, a probability exists that a trajectory of a robotic arm may intersect the position of the surgeon. A collision between the surgeon and the robotic arm and/or related instruments is an adverse event experienced in the related art and should be avoided in order to preserve the sterile field. A collision between the surgeon and the robotic arm and/or related instruments may further result in injury to a patient, a surgeon, or other medical personnel who are present. The probability that a collision will occur is increased in medical procedures with multiple clinical staff are disposed in, or cross, the optical camera's line of sight.

In yet other related art tracking systems, a tracking sphere is used in conjunction with a tracking camera to merely calculate the distance between tracked tools within the surgical workspace.

Accordingly, challenges experienced in the related art include surgical navigation systems that are unduly cumbersome, that provide inaccurate tracking of items, and that are unable to prevent accidental collisions between items and/or personnel in the surgical theatre. The movement of the robotic arm within the operating room may interfere with the medical procedure, the physicians, and the surgical team. Such interference may negatively impact the procedure or harm the patient. Therefore, a need exists for apparatuses and methods that facilitate restricting the movement of the robotic arm.

SUMMARY

During a medical procedure, a surgical navigation system may operate to track medical instruments relative to a reference point. The surgical navigation system may also be used to define, spatially, an area or volume within the operating room ("OR") within which the robotic arm should not enter. The surgical navigation system tracks instruments and determines their location relative to the reference point. The surgical navigation system also detects changes in the location of the tracked instrument relative to the reference point. The change data may identify a safety zone within the OR. The navigation system may also extrapolate the change data to define the safety zone. Movement of the robotic arm within the safety zone is restricted.

The disclosed system permits users of the system to define one or more safety zones within which the robotic arm's movement is restricted using a naturally intuitive method. Further, since the spatially defined safety zone is defined relative to the reference point, the safety zone is spatially shifted within the OR if the reference point moves. In one example, the reference point is positioned on the patient; thereby allowing the user to define a region around the patient within which the robotic arm will not enter. In another example, the reference point is associated with a tracked clinical instrument; thereby allowing the user to define a region around the clinical instrument. Defining such safety zones will reduce or prevent collisions with the robotic arm resulting from movement of the robotic arm.

One aspect of the present disclosure provides a method for identifying a safety zone, using a medical navigation system, for restricting movement of a robotic arm in an operating room, the method comprising receiving, at the medical navigation system, an initiation input indicating initiation of defining of the safety zone; in response to receiving the initiation input, tracking an instrument using the medical navigation system, determining a location of the tracked instrument relative to a reference point, and detecting changes in the location of the tracked instrument until a termination input is received at the medical navigation system, the termination input indicating termination of the defining of the safety zone; and storing, in memory, change data indicative of the changes in the location of the tracked instrument, the data identifying the a spatial position and meta data (e.g. the time that it was established, etc.) of the safety zone relative to the reference point.

Another aspect of the present disclosure provides a medical navigation system comprising a tracking system; a processor; and memory, coupled to the processor and storing instructions for identifying a safety zone for restricting movement of a robotic arm in an operating room, wherein the processor is configured to receive an initiation input indicating initiation of defining of the safety zone; in response to receiving the initiation input, track an instrument using the tracking system, determine a location of the tracked instrument relative to a reference point, and detect changes in the location of the tracked instrument until a termination input is received at the medical navigation system, the termination input indicating termination of the defining of the safety zone; and store, in memory, change data indicative of the changes in the location of the tracked instrument, the data identifying the a spatial position of the safety zone relative to the reference point.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIGS. 7A-7B illustrate side plan views of exemplary embodiments of gesture instruments for identifying the safety zone, in accordance with an embodiment of the present disclosure;

Similar reference numerals are used in different Figures to denote similar components.

DETAILED DESCRIPTION

The systems and methods described herein are useful in the field neurosurgery, including oncological care, neurodegenerative disease, stroke, brain trauma, prostate surgery, gynecological surgery, and orthopedic surgery. However, the subject matter of the present disclosure may extend or apply to other conditions or fields of medicine; and such extensions or applications are encompassed by the present disclosure. The systems and methods described herein encompass surgical processes that are applicable to surgical procedures for brain, spine, knee, and any other region of the body that will benefit from the use of an access port or small orifice to access the interior of an animal body, such as a human body.

Various systems, apparatuses, devices, or processes are below-described and provide examples of the navigation systems and methods embodiments, in accordance with embodiments of the present disclosure. None of the below-described embodiments limits any claimed embodiment; and any claimed embodiment may also encompass systems, apparatuses, devices, or processes which may differ from below-described examples. The claimed embodiments are not limited to systems, apparatuses, devices, or processes having all of the features of any one of the below-described systems, apparatuses, devices, or processes or to features common to some or all of the below-described systems, apparatuses, devices, or processes.

Furthermore, this Detailed Description sets forth numerous specific details in order to provide a thorough understanding of the various embodiments described throughout the present disclosure. However, it will be understood by those of ordinary skill in the art that the embodiments described herein may be practiced without these specific details. In other instances, well-known methods, procedures and components have not been described in detail so as not to obscure the embodiments described herein.

Figure 1:
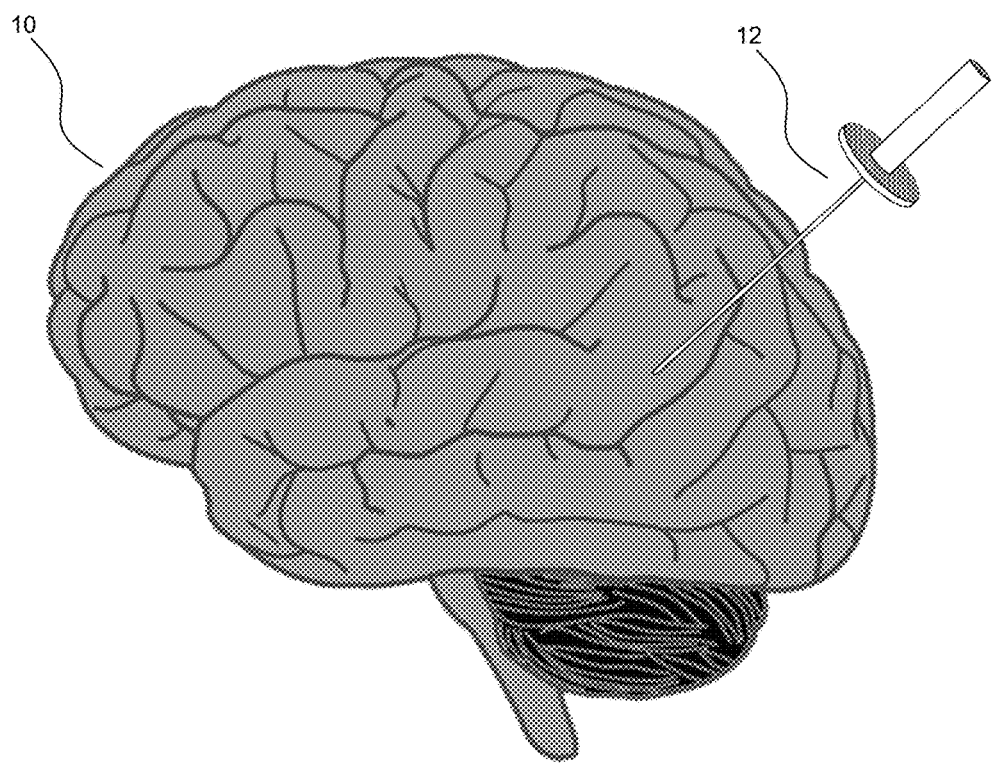
FIG. 1 illustrates a perspective view of an access port inserted into a human brain for providing access to internal brain tissue, in accordance with the related art.
Figure 2:
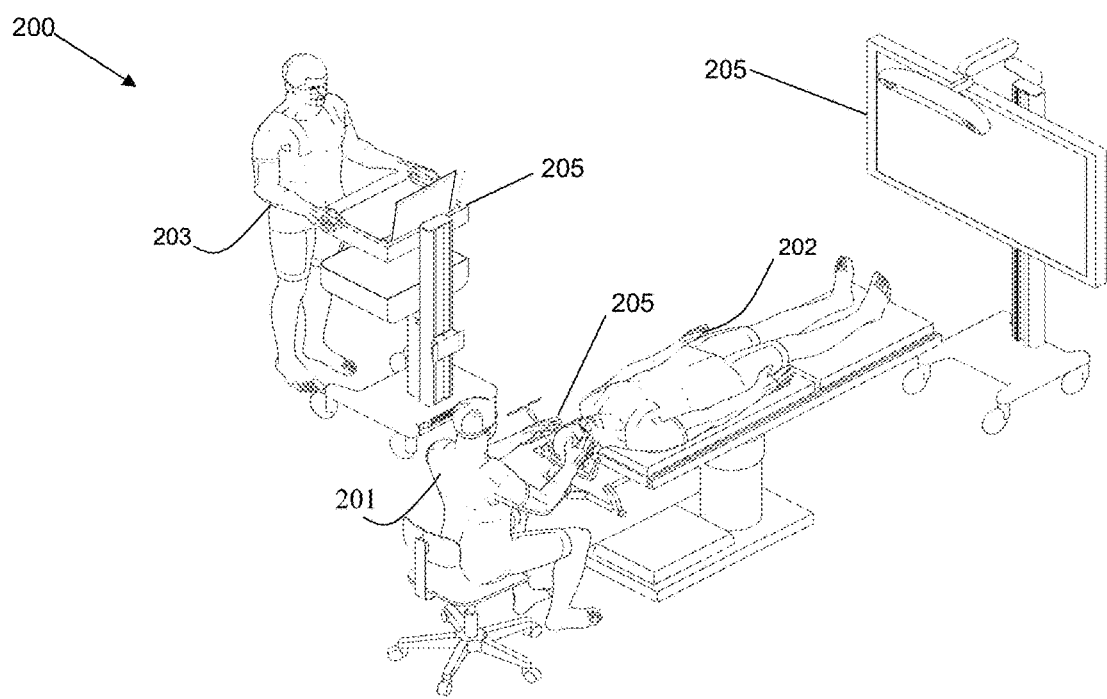
FIG. 2 illustrates a perspective view of a navigation system for use in performing a medical procedure, such as a minimally invasive access port-based surgery, in accordance with an embodiment of the present disclosure.

Referring to FIG. 2, this diagram illustrates, in a perspective view, a navigation system 200 for use in performing a medical procedure, such as a minimally invasive access port-based surgery, e.g., navigated image-guided surgery, in accordance with an embodiment of the present disclosure. By example only, a surgeon 201 conducts a surgery on a patient 202 in an OR environment. A medical navigation system 200 comprises: an equipment tower 200a, a tracking system for tracking at least one object, such as at least one of a surgical tool, a surgical device, medical equipment, and the like, and at least one subject, such at least one of: at least one patient 202, e.g., involving a live tissue donor (some organ transplants, kidneys or lungs) or bone marrow transplants (cancer patients), and at least one medical personnel, e.g., surgeons, anesthesiologists, pathologists, nurses, and the like, in the OR, at least one display device 205, the tracking system facilitating performing a medical procedure. A medical navigation system 200 is further configured for interaction with an operator 203 for facilitating operation, control, and assistance in relation to the tracking system and/or the at least one display device 205.

Figure 3A:
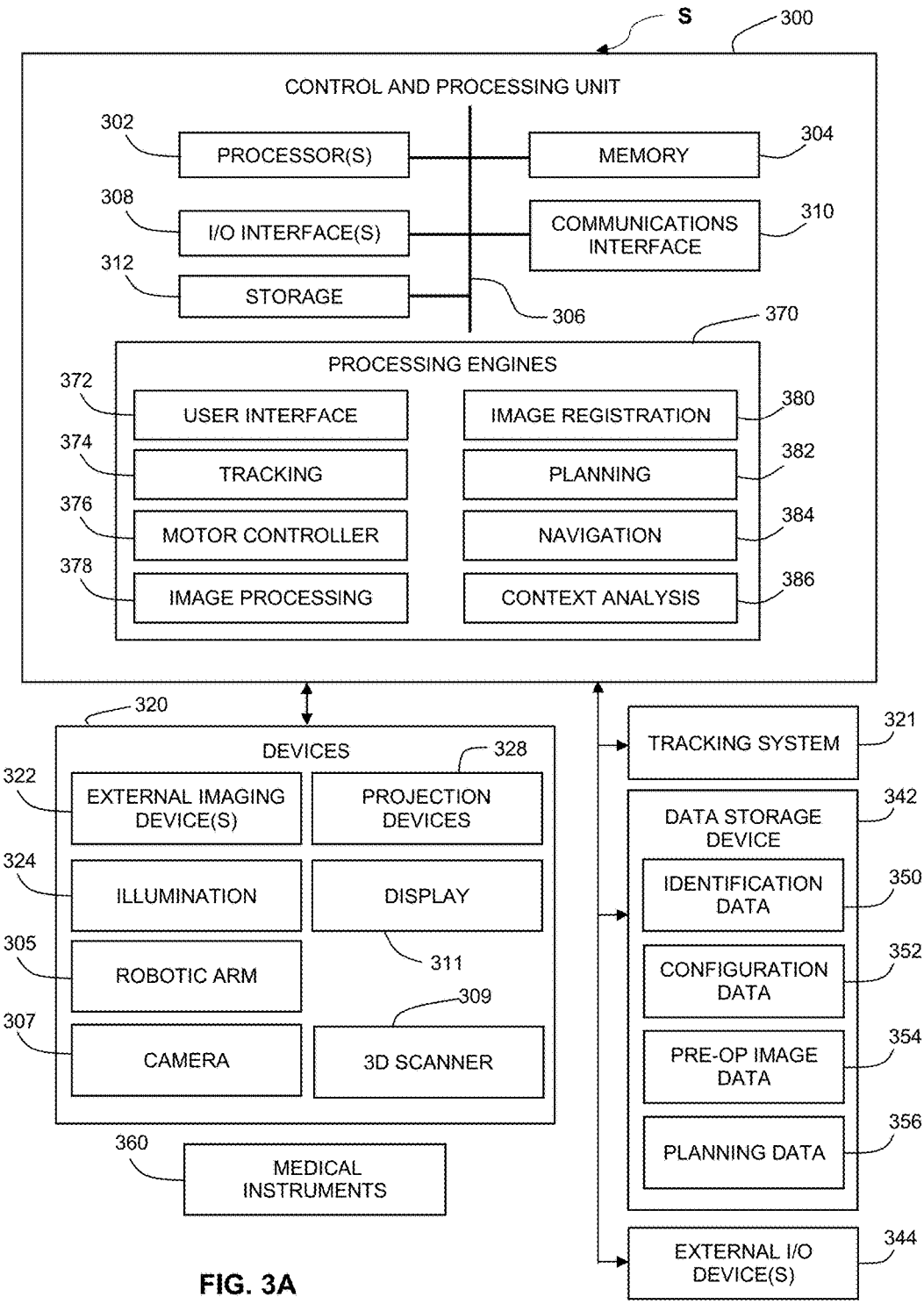
FIG. 3A is a block diagram illustrating a control and processing system or unit for use in the navigation system, as shown in FIG. 2, for performing a medical procedure, in accordance with an embodiment of the present disclosure.

Referring to FIG. 3A, this block diagram illustrates a control and processing system or unit 300 for use in the navigation system 200, as shown in FIG. 2, for performing a medical procedure, in accordance with an embodiment of the present disclosure. By example only, the control and processing system 300 comprises at least one processor 302, a memory 304, a system bus 306, at least one input/output (I/O) interface 308, a communication interface 310, and a storage device 312. The control and processing system 300 is interfaceable with other external devices, such as a tracking system 321, data storage 342, and external user input and output devices 344, which may comprise, for example, at least one of a display, a keyboard, a mouse, sensors attached to medical equipment, a foot pedal, a microphone, and a speaker.

Still referring to FIG. 3A, data storage 342 comprises any suitable data storage device, such as a local or remote computing device, e.g., a computer, a hard drive, a digital media device, and a server, the data storage device configured to store a database. For example, the data storage device 342 is configured to store identification data 350 for identifying at least one medical instrument 360 and configuration data 352 that associates customized configuration parameters with at least one medical instrument 360. Data storage device 342 may also include preoperative image data 354 and/or medical procedure planning data 356. Although data storage device 342 comprises a single device by example only; however, understood is that, in other embodiments, data storage device 342 comprises a plurality of storage devices 342.

Still referring to FIG. 3A, medical instruments 360 are identifiable by the control and processing system 300. Medical instruments 360 are capable of coupling with and are controllable by the control and processing unit 300. Alternatively, the medical instruments 360 are operable, or otherwise employed, independent of the control and processing unit 300. The tracking system 321 tracks at least one medical instrument 360 and spatially registers the at least one medical instrument 360 in relation to an intra-operative reference frame. For example, the medical instruments 360 comprise tracking spheres recognizable by a tracking camera 307. In one example, the tracking camera 307 comprises an infrared (IR) tracking camera. In another example, as sheath placed over a medical instrument 360 is couple-able with, and controlled by, the control and processing unit 300. The control and processing unit 300 is also interfaceable with a number of configurable devices, and may intra-operatively reconfigure at least one such device based on configuration parameters obtained from the configuration data 352. Examples of the devices 320, include at least one external imaging device 322, at least one illumination device 324, a robotic arm 305 (see FIGS. 3B-3C), at least one projection device 328, a display 211, and a 3-D scanner 309.

Still referring to FIG. 3A, the control and processing unit 300 can be implemented via processor(s) 302 and/or memory 304. For example, the functionalities described herein can be partially implemented via hardware logic in the processor 302 and partially using the instructions stored in memory 304, at least one processing module, or an engine 370. Example processing modules include, but are not limited to, a user interface engine 372, a tracking module 374, a motor controller 376, an image processing engine 378, an image registration engine 380, a procedure planning engine 382, a navigation engine 384, and a context analysis module 386. While the example processing modules are shown separately, the processing modules 370 may be stored in the memory 304; and the processing modules 370 may be collectively referred to as processing modules 370.

Still referring to FIG. 3A, that the system 300 is not limited to the components as shown herein. The control and processing system 300 may comprise an external component or device. In one example, a navigation module 384 comprises an external navigation system that can be integrated with the control and processing system 300. Some embodiments of the system 300 are implementable by using a processor 302 without using additional instructions stored in the memory 304. Some embodiments of the system 300 are implementable by using the instructions stored in the memory 304 for execution by at least one general purpose microprocessors. Thus, the present disclosure is not limited to a specific configuration of hardware and/or software, but encompasses any configuration of hardware, firmware, and/or software.

Still referring to FIG. 3A, while some embodiments of the present disclosure are implementable in fully functioning computers and computer systems, various embodiments are capable of being distributed as a computing product in a variety of forms and are capable of being applied regardless of the particular type of machine or computer readable media used to actually effect the distribution. At least some aspects disclosed can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device.

Still referring to FIG. 3A, in some embodiments, a computer readable storage medium is used to store software and data which, when executed by a data processing system, causes the system to perform various methods. The executable software and data may be stored in various places including for example ROM, volatile RAM, nonvolatile memory and/or cache. Portions of this software and/or data may be stored in any one of these storage devices. Examples of computer-readable storage media include, but are not limited to, recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions may be embodied in digital and analog communication links for electrical, optical, acoustical or other forms of propagated signals, such as carrier waves, infrared signals, digital signals, and the like.

The storage medium may be the internet cloud, or a computer readable storage medium such as a disc.

Still referring to FIG. 3A, at least some of the methods described herein are capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

Still referring to FIG. 3A, according to one aspect of the present disclosure, the navigation system 200, comprising the control and processing unit 300, provides tools to the neurosurgeon that will lead to the most informed, least damaging neurosurgical operations. In addition to removal of brain tumors and intracranial hemorrhages ('ICH'), the navigation system 200 can also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, aspects of the present disclosure may be applied to any suitable medical procedure.

Figure 3B:
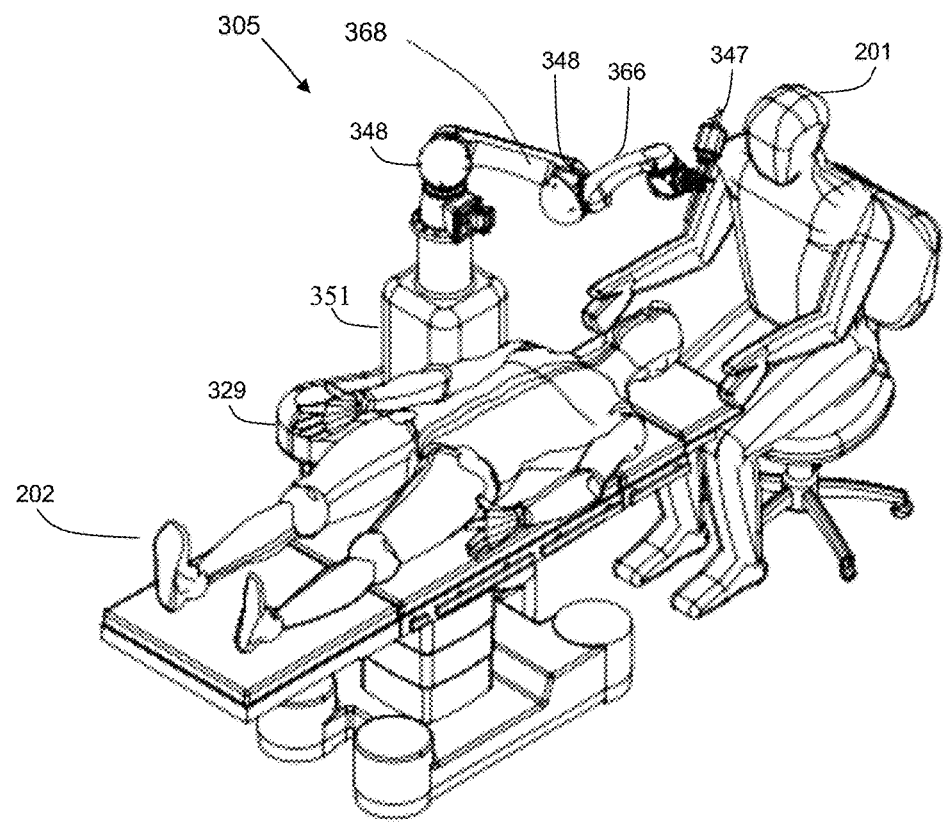
FIGS. 3B and 3C illustrate a perspective view of a robotic arm for use in performing a medical procedure, such as a minimally invasive access port-based surgery, in accordance with an embodiment of the present disclosure.
Figure 3C:
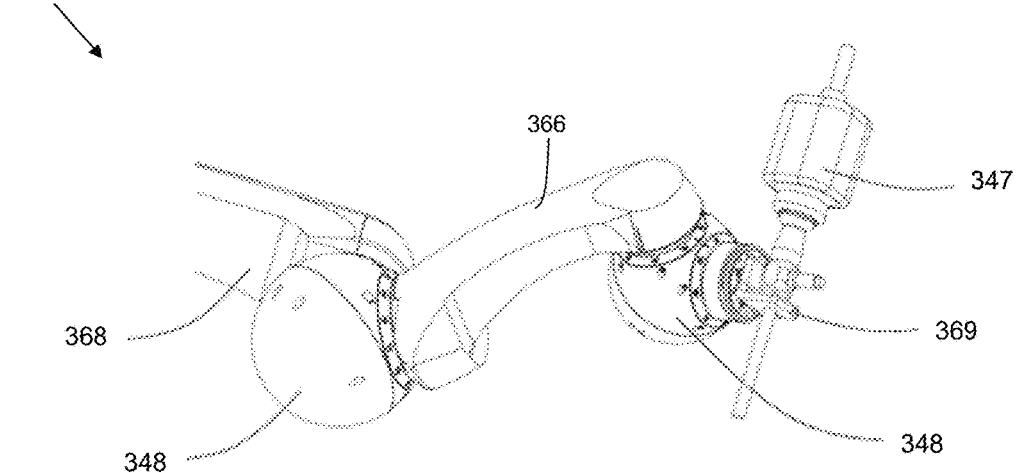

FIGS. 3B-3C show three-dimensional perspective drawings of an example embodiment of robotic arm 305. Robotic arm 305 includes first and second linkages 368, 366 and end effector 347. The first and second linkages 368, 366 allow robotic arm 305 to extend across patient 202, as shown in FIG. 3B. Further, as shown in FIG. 3C, first and second linkages 368, 366 are joined to one another by a first joint 348. The angle at which first and second linkages 368, 366 are jointed may be controlled electronically by first joint 348. Similarly, second linkage 368 and end effector 347 are joined to one another by a second joint 348, and the angle at which second linkage 366 and end effector 347 are jointed may be controlled electronically by second joint 348. First and second joints 348 provide redundant number of degrees of freedom to allow for easy movement of end effector 347.

Still referring to FIG. 3B-3C, end effector 347 has a distal end 369. As previously illustrated, distal end 369 may have connectors that can rigidly hold an imaging device while facilitating easy removal of the device to interchange with other imaging devices. Distal end 369 may also be tracked using navigation system 200 (FIG. 2) by attaching tracking markers thereto (not shown).

Still referring to FIG. 3B-3C, robotic arm 305 also has a base 329 providing a mechanically stable system to balance the load of the arm. Base 329 may have attached thereto caster wheels to facilitate mobility of the arm across the room. Also attached to base 329 is frame 351, which raises (along a vertical axis) first and second linkages 368, 366 and end effector 347 of robotic arm 305. Frame 351 may be fixed one height, or alternatively may include a lifting mechanism (e.g. pneumatic piston) to allow for the height of robotic arm 305 to be adjusted.

Each joint may have any number of configurable positions (e.g. positions A, B, C, D, E, and so forth). The angles of three joints 348, along with the degree of extension of frame 351, may be defined by an array of joint angles. Each array of joint angles corresponds to a particular spatial position within the OR of distal end 369, which may be tracked using medical navigation system 200. Accordingly, system 300 may define an array of joint angles to define a particular spatial position at which distal end 369 should be located. Furthermore, system 300 may compute the geometric shape of robotic arm 305 based on a model of the arm taking as input an array of joint angles, or alternatively, retrieve from a database the geometric shape of robotic arm 305 based on the array of joint angles.

It should be noted that while FIGS. 3B-3C illustrate a floor-standing design, other configurations may be employed. For example, alternative example configurations include a structure that is supported from the ceiling of the operating room; a structure extending from a tower intended to encase imaging instrumentation; and by rigidly attaching the base of the automated arm to the surgical table.

In some embodiments, multiple arms may be used simultaneously for one procedure and navigated from a single system. In such an embodiment, each distal end may be separately tracked so that the orientation and location of the devices is known to the intelligent positioning system and the position and/or orientation of the mounted distal end devices may be controlled by actuating the individual automated arms based on feedback from the tracking system. This tracking can be performed using any of the methods and devices disclosed herein.

Figure 4A:
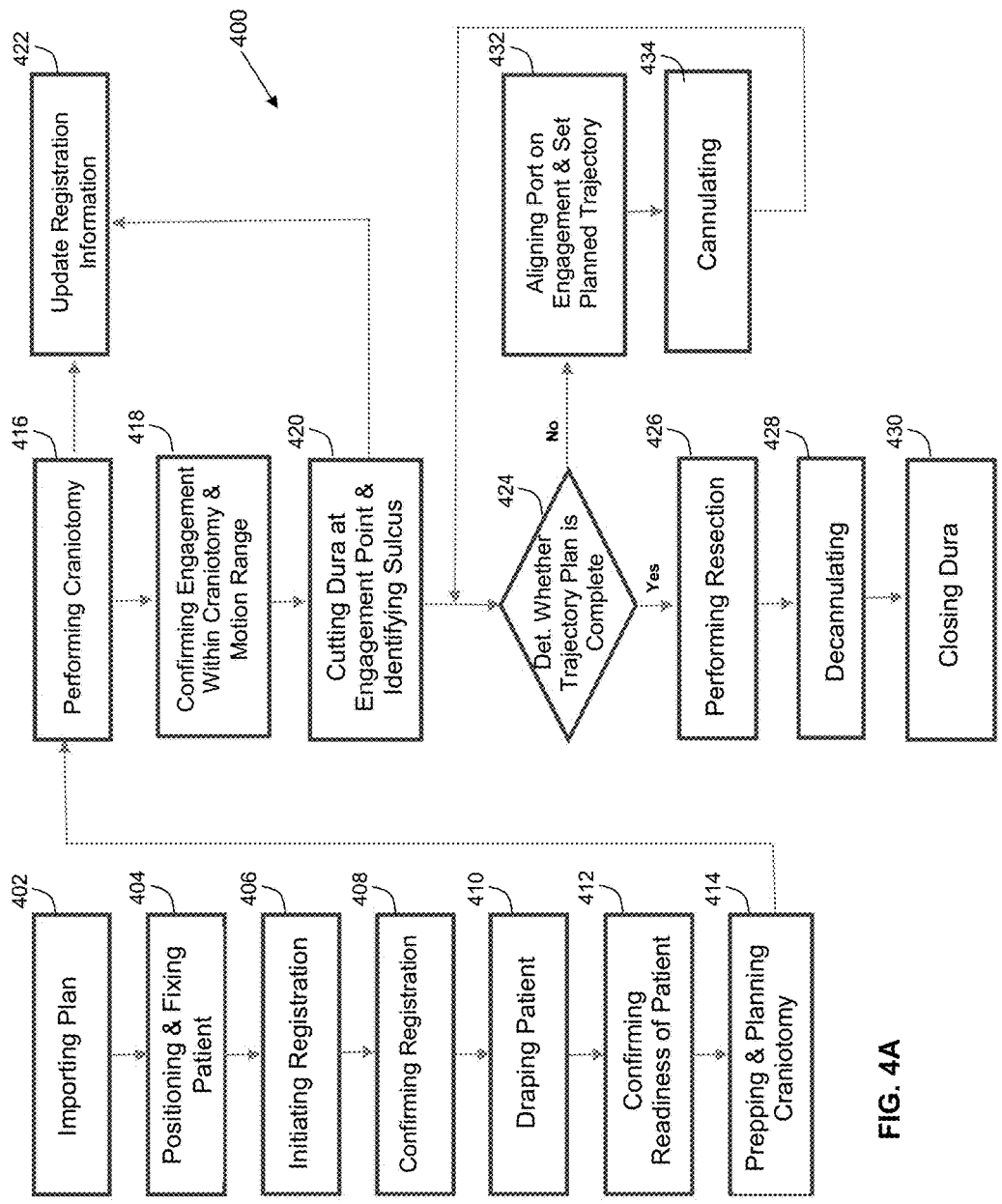
FIG. 4A is a flow chart illustrating a method of using the navigation system, as shown in FIG. 2, comprising the control and processing system, as shown in FIG. 3, for performing a medical procedure, in accordance with an embodiment of the present disclosure.

Referring to FIG. 4A, this flow chart illustrates a method 400 of using the navigation system 200, as shown in FIG. 2, comprising the control and processing system 300, as shown in FIG. 3A, for performing a medical procedure, in accordance with an embodiment of the present disclosure. The medical procedure may comprise a port-based surgical procedure. The method 400 comprises: importing a port-based surgical plan, as indicated by block. A detailed description of the process to create and select a surgical plan is outlined in international publication WO/2014/139024, entitled "PLANNING, NAVIGATION AND SIMULATION SYSTEMS AND METHODS FOR MINIMALLY INVASIVE THERAPY," claiming priority to U.S. Provisional Patent Application Ser. Nos. 61/800,155 and 61/924,993, all of which are hereby incorporated by reference in their entirety.

Still referring to FIG. 4A, once the plan has been imported into the navigation system 200, as indicated by block 402, the method 400 further comprises positioning and affixing the patient is affixed into position by using a body holding mechanism, as indicated by block 404, wherein positioning and affixing comprises confirming that the head position is consistent with the patient plan in the navigation system 200. For example, a computer or controller, forming part of the equipment tower 200a of medical navigation system 200, is configurable to implement confirming that the head position is consistent with the patient plan in the navigation system 200.

Still referring to FIG. 4A, the method 400 further comprises initiating registration of the patient, as indicated by block 406. The phrase "registration" or "image registration" refers to the process of transforming different sets of data into one coordinate system. Data may include multiple photographs, data from different sensors, times, depths, or viewpoints. The process of "registration" is used in the present application for medical imaging in which images from different imaging modalities are co-registered. Registration is used in order to be able to compare or integrate the data obtained from these different modalities.

Still referring to FIG. 4A, initiating registration of the patient, as indicated by block 406, of the method 400 encompasses at least one of numerous registration techniques. Non-limiting examples include intensity-based methods that compare intensity patterns in images via correlation metrics, while feature-based methods find correspondence between image features such as points, lines, and contours. Image registration methods may also be classified according to the transformation models they use to relate the target image space to the reference image space. Another classification can be made between single-modality and multi-modality methods. Single-modality methods typically register images in the same modality acquired by the same scanner or sensor type, for example, a series of magnetic resonance (MR) images may be co-registered, while multi-modality registration methods are used to register images acquired by different scanner or sensor types, for example in magnetic resonance imaging and positron emission tomography (PET). In the present disclosure, multi-modality registration methods may be used in medical imaging of the head and/or brain as images of a subject are frequently obtained from different scanners. Examples include registration of brain computerized tomography (CT)/MRI images or PET/CT images for tumor localization, registration of contrast-enhanced CT images against non-contrast-enhanced CT images, and registration of ultrasound and CT.

Still referring to FIG. 4A, the method 400 further comprises: confirming registration, as indicated by block 408; draping the patient, as indicated by block 410; confirming readiness of the patient, as indicated by block 412; preparing and planning a craniotomy, as indicated by block 414; cutting a cranium, thereby performing the craniotomy, as indicated by block 416, and updating registration information, as indicated by block 422; confirming engagement within a space defined by the craniotomy and a range of motion, as indicated by block 418; cutting dura at an engagement point and identifying sulcus, as indicated by block 420, and updating registration information, as indicated by block 422; determining whether a trajectory plan is complete, as indicated by block 424, and, if so, performing a resection, as indicated by block 436, decannulating, as indicated by block 428, and closing dura, as indicated by block 430; and, if not, aligning the port on an engagement point and setting the port, as indicated by block 432, cannulating, as indicated by block 434, and determining whether a trajectory plan is complete, as indicated by block 424.

Figure 4B:
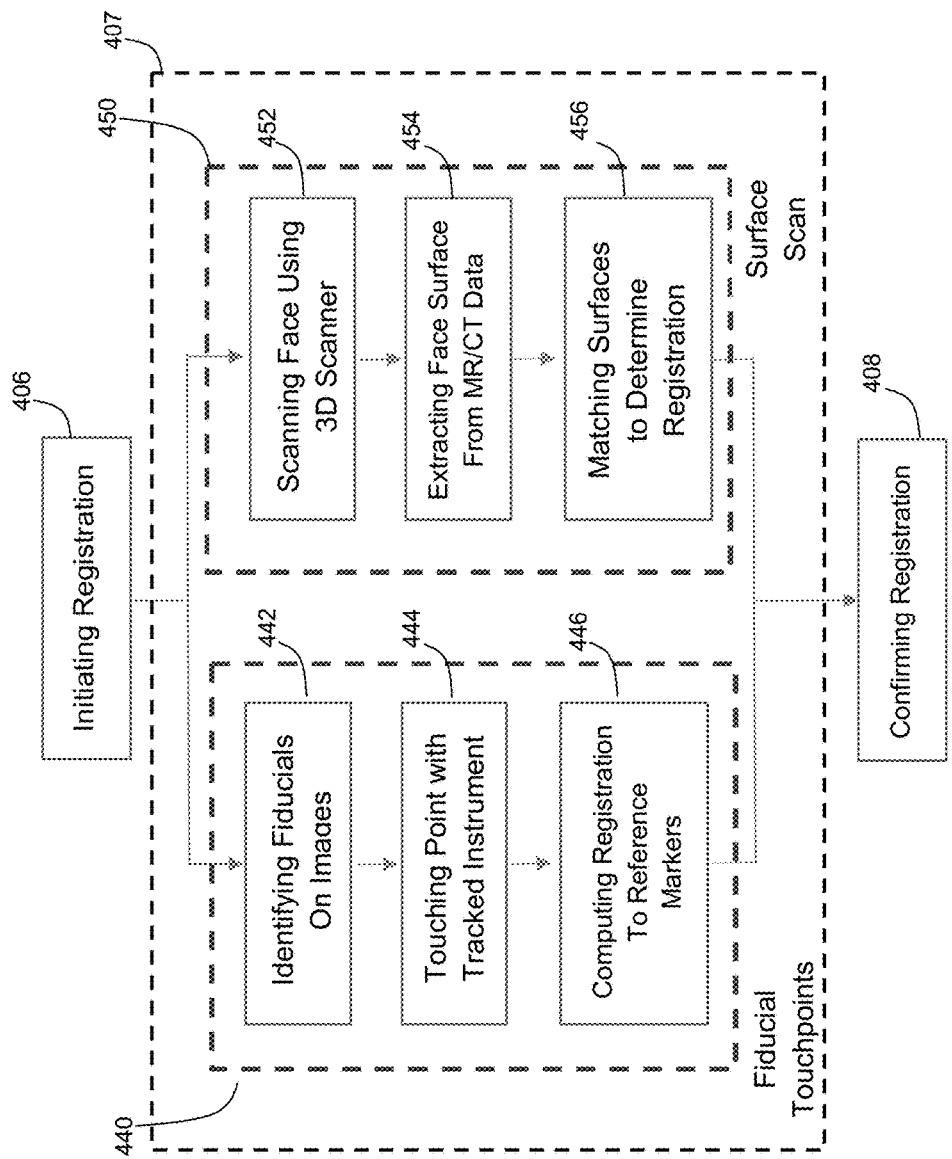
FIG. 4B is a flow chart illustrating a method of registering a patient, such as after initiating registration and before confirming registration, as shown in FIG. 4A, for performing a medical procedure by way of the navigation system, in accordance with an embodiment of the present disclosure.

Referring to FIG. 4B, this flow chart illustrates a method 407 of registering a patient, such as after initiating registration, as indicated by 406, of the method 400, and before confirming registration, as indicated by block 408, of the method 400, as shown in FIG. 4A, for performing a medical procedure by way of the navigation system 200, in accordance with an embodiment of the present disclosure. The method 400 further comprises the method 407, in accordance with an embodiment of the present disclosure. If the use of fiducial touch points is contemplated, the method 407 involves performing fiducial steps, as indicated by block 440, comprising: identifying fiducials, fiducial markers, or reference markers on images, as indicated by block 442, touching the touch points with a tracked instrument, as indicated by block 444; and computing the registration to reference markers by way of the navigation system, as indicated by block 446.

Still referring to FIG. 4B, if the use of fiducial touch points is not contemplated, e.g., if a surface scan is alternatively contemplated, the method 407 involves performing surface scan steps, as indicated by block 450, comprising: scanning a face by way of a 3-D scanner, thereby providing in situ scanned face data, as indicated by block 452; extracting the face surface from MR/CT data scanner, as indicated by block 454; and matching the in situ scanned face data with the extracted face data to determine whether registration is sufficient by way of a plurality of data points, as indicated by block 456. Upon completion of either the method 440 or the method 450, the method 400 comprises confirming registration by using the data extracted for computation, as indicated by block 408, as shown in FIG. 4A.

Referring back to FIG. 4A, after confirming registration by using the data extracted for computation, as indicated by block 408, the method 400 comprises draping the patient, as indicated by block 410. Typically, draping involves covering the patient and surrounding areas with a sterile barrier to create and maintain a sterile field during the surgical procedure. The purpose of draping is to eliminate the passage of microorganisms, e.g., bacteria, viruses, or prions, between non-sterile and sterile areas.

Still referring back to FIG. 4A, upon completion of draping (block 410), the patient engagement points are confirmed (block 412) and then the craniotomy is prepared and planned (block 414). Upon completion of the preparation and planning of the craniotomy (block 414), the craniotomy is cut and a bone flap is temporarily removed from the skull to access the brain (block 416). Registration data is updated with the navigation system at this point (block 422). The engagement within craniotomy and the motion range are confirmed (block 418). The procedure advances to cutting the dura at the engagement points and identifying the sulcus (block 420). The cannulation process is initiated (block 424). Cannulation involves inserting a port into the brain, typically along a sulci path as identified at block 420, along a trajectory plan. Cannulation is typically an iterative process that involves repeating the steps of aligning the port on engagement and setting the planned trajectory (block 432) and then cannulating to the target depth (block 434) until the complete trajectory plan is executed (block 424).

Still referring back to FIG. 4A, once cannulation is complete, the surgeon then performs resection (block 426) to remove part of the brain and/or tumor of interest. The surgeon then decannulates (block 428) by removing the port and any tracking instruments from the brain. Finally, the surgeon closes the dura and completes the craniotomy (block 430). Some aspects of the method 400 are specific to port-based surgery, such portions of the steps indicated by blocks 428, 420, and 434, but the appropriate portions of the steps indicated by blocks 428, 420, and 434 are optionally performed or suitably modified when performing non-port based surgery.

Still referring back to FIG. 4A, when performing a surgical procedure using the navigation system 200, as shown in FIGS. 4A and 4B, the navigation system 200 acquires and maintains a reference of the location of the tools in use as well as the patient in three dimensional (3-D) space. In other words, during a navigated neurosurgery, a tracked reference frame is used that is fixed relative to the patient's skull. During the registration phase of a navigated neurosurgery, e.g., as indicated by block 406, as shown in FIGS. 4A and 4B, a transformation is calculated that maps the frame of reference of preoperative MRI or CT imagery to the physical space of the surgery, specifically the patient's head. This mapping may be accomplished by the navigation system 200 tracking locations of fiducial markers fixed to the patient's head, relative to the static patient reference frame. The patient reference frame is typically rigidly attached to the head fixation device, such as a Mayfield clamp. Registration is typically performed before the sterile field has been established, e.g., by performing the step indicated by block 410.

Still referring back to FIG. 4A, the method 400 overcomes many related art problems. For instance, most related art navigation systems require the patient reference be exchanged during the draping phase and the original patient reference frame used for registration is replaced with a sterile patient reference frame. This related art exchange can cause a loss of accuracy. Other related art systems may require the non-sterile reference frame to be draped with a sterile, transparent plastic surgical drape. Where tracking spheres are used in conjunction with an infrared (IR) tracking camera, visibility through this drape can cause optical distortion of the measured reference position and can cause loss of accuracy. This process is also operator and set-up dependent, being affected by how the sterile drape is positioned and how tightly it is formed around the reference frame.

Still referring back to FIG. 4A, the method 400 overcomes many other related art problems. For instance, throughout a navigated surgery, the patient reference frame is sometimes bumped by the surgeon or others involved into the procedure. A bump that is strong enough could cause a shift in the frame's location and therefore create a misregistration. In order to address the shortcomings of conventional systems outlined above, according to one aspect of the present disclosure, a patient reference design is provided that incorporates a removable sterile cover. According to another aspect of the present description, a sensor may be attached to, or embedded in, the patient reference frame to provide the medical navigation system 200 with information that can be used to determine whether the patient reference frame is bumped with enough force such that the frame's location requires re-registration.

Still referring back to FIG. 4A, the draping step of the method 400 comprises using a sterile drape having a plastic lens that is placed over the patient face, the plastic lens containing the tracking markers. In one example, the sterile cover maybe a substantially rigid lens. In one example, the markers could be active IR markers or passive reflective spheres. The sterile cover may not cause significant distortion like a standard drape would. The sterile cover may have a transparent plastic sock that extends downward from the cover to cover the rest of the patient reference and patient reference mounting arm and extension. The patient reference may be designed to permit +/−45 degree line-of-sight between the tracking camera 307 (e.g., a Northern Digital Polaris Spectra) and the patient reference. The navigation system 200 further comprises force sensors and/or accelerometers, either wired or wirelessly; and the navigation system 200 may display a warning and/or force re-registration if too great of a force and/or acceleratio3n is imparted on the patient reference.

Figure 5B:
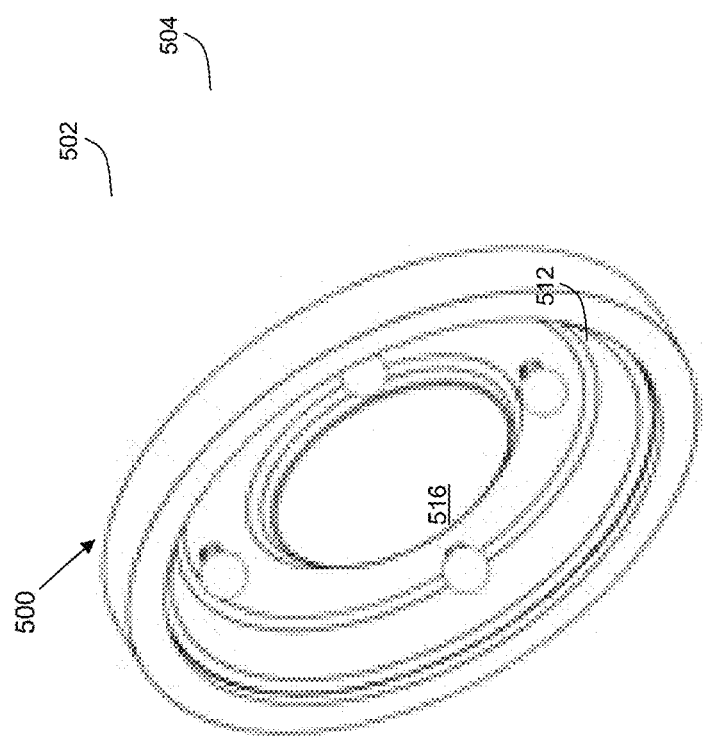
FIG. 5B illustrates a perspective view of the patient reference device, as shown in FIG. 5A, comprising a cover and a housing, for performing a medical procedure by way of the navigation system, in accordance with an embodiment of the present disclosure.
Figure 5A:
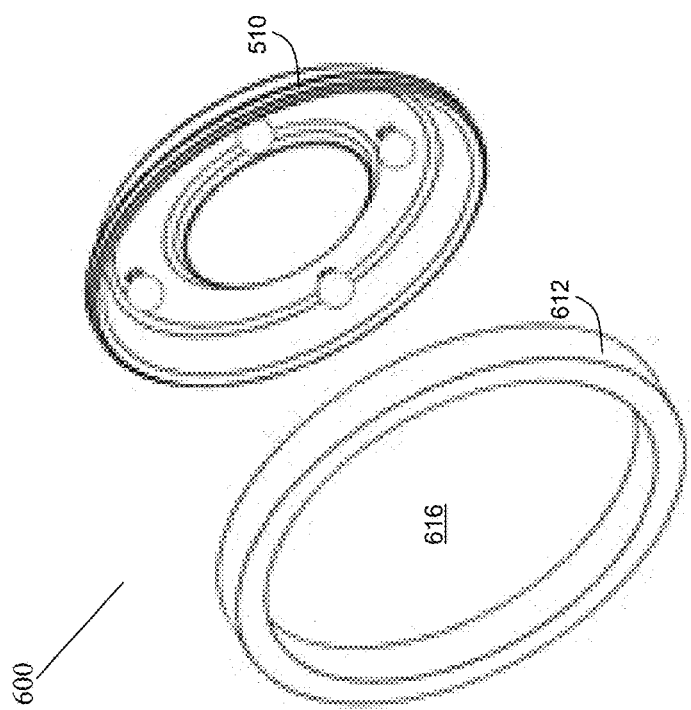
FIG. 5A illustrates an exploded perspective view of a patient reference device, comprising a cover and a housing, for performing a medical procedure by way of the navigation system, in accordance with an embodiment of the present disclosure.

Referring to FIG. 5A, this diagram illustrates, in an exploded perspective view, a patient reference device 500, comprising a cover 512 and a housing 502, for performing a medical procedure by way of the navigation system 200, in accordance with an embodiment of the present disclosure.

Referring to FIG. 5B, this diagram illustrates, in a perspective view, the patient reference device 500, as shown in FIG. 5A, comprising a cover 512 and a housing 502, for performing a medical procedure by way of the navigation system 200, in accordance with an embodiment of the present disclosure.

Figure 5C:
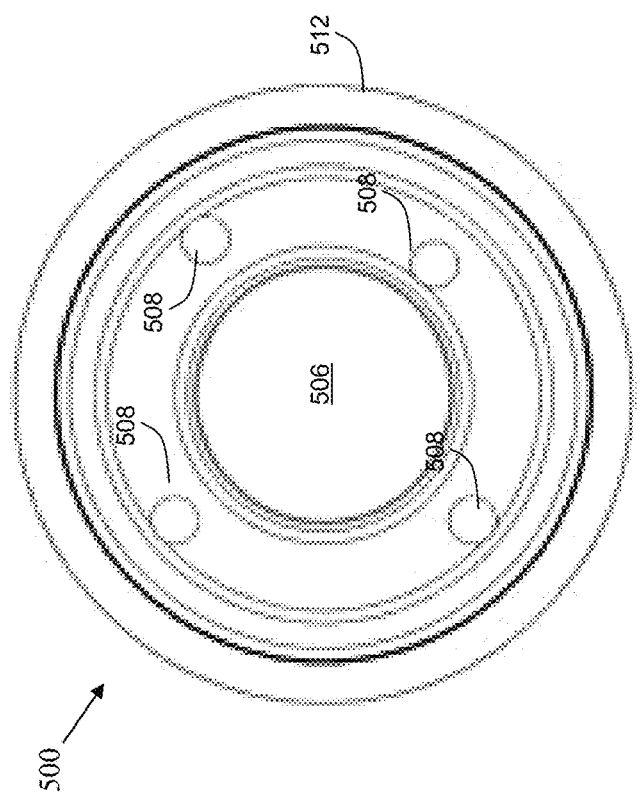
FIG. 5C illustrates a front view of the patient reference device, as shown in FIGS. 5A and 5B, comprising a cover and a housing, for performing a medical procedure by way of the navigation system, in accordance with an embodiment of the present disclosure.

Referring to FIG. 5C, this diagram illustrates, in a front view, the patient reference device 500, as shown in FIGS. 5A and 5B, comprising a cover 512 and a housing 502, for performing a medical procedure by way of the navigation system 200, in accordance with an embodiment of the present disclosure. The patient reference device 500 has a drape attached, wherein the drape has a window with a plurality of tracking markers 508, such as tracking spheres.

Figure 5D:
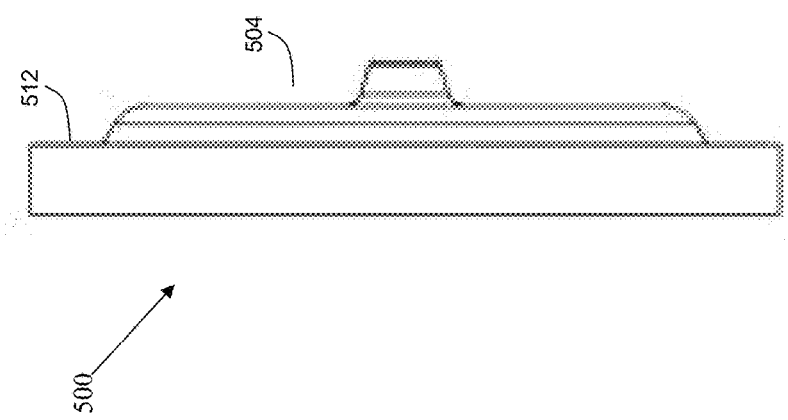
FIG. 5D illustrates a side view of the patient reference device, as shown in FIGS. 5A and 5B, comprising a cover and a housing, for performing a medical procedure by way of the navigation system, in accordance with an embodiment of the present disclosure.

Referring to FIG. 5D, this diagram illustrates, in a side view, the patient reference device 500, as shown in FIGS. 5A and 5B, comprising a cover 512 and a housing 502, for performing a medical procedure by way of the navigation system 200, in accordance with an embodiment of the present disclosure. The patient reference device 500 is configured for attaching a drape (not shown).

Referring back to FIGS. 5A-5D, the patient reference device 500 comprises a housing 502 having a back side 504 and a front side 506, by example only, at least three tracking markers 508 are attached to the front side 506 of the housing 502. In another example, four or more tracking makers 508 may be used. The tracking markers 508 each comprise a top 514, generally on the opposite side in relation to a portion of the tracking markers 508 that attach to the housing 502. While an example of either three or four tracking markers 508 is provided, any number of tracking markers 508 may be used for a particular application and is encompassed by the present disclosure. In one example, only one or two tracking markers may be used. In another example, the tracking markers 508 comprise passive reflective tracking spheres or active infrared (IR) markers that may be visible to a tracking camera, such as the tracking camera 307 of the navigation system 200. In another example, the tracking markers 508 may be active light emitting diodes (LEDs) or a graphical pattern printed on a three dimensional (3-D) structure used by a vision system such as the tracking camera to acquire 6 degrees of freedom (DOF).

Still referring back to FIGS. 5A-5D, the housing 502 is generally disc shaped; however, any suitable shaped housing or frame may be used for a particular application and is encompassed by the present disclosure. In some examples, the housing 502 comprises a solid member, either square shaped or disc shaped and the frame may further have superfluous material removed that is not important to the structural integrity of the housing, e.g., the housing comprises generally square shape or a disc shape with holes formed therein. In one example, the housing 502 comprises a metal, such as machined aluminum, blasted with aluminum oxide, e.g., 180-grit, and then hard anodized. Both the blasting and anodization processes provide a matte finish of the housing 502 whereby unwanted reflection is minimized to facilitate tracking by the tracking camera. Naked metallic surfaces or even plastic sometimes lead to poor accuracy for camera based tracking systems due to the presence of reflection, which can be further magnified with the use of a plastic drape on the patient reference 500. In the present disclosure, the exemplary blasted and anodized aluminum finish improves tracking performance of the tracking camera without degrading accuracy. While one example of a suitable finish for the housing 502 is provided, any suitable finish of low reflectivity may be used to meet the design criteria of a particular application. In another example, the housing 502 comprises any suitable type of plastic or metal.

Still referring back to FIGS. 5A-5D, the housing 502 extends along the back side 504 of the housing 502. The housing 502 further extends beyond a horizontal plane defined by the tops 514 of the tracking markers 508. The housing terminates at an edge 510. In one example, the edge 510 may be substantially continuous, such as forming a shape such as a circle, a square, an oval, or a rectangle in one plane. A sterile cover 512 may be attached to the substantially continuous edge 510 of the housing 502 for covering the housing 502 and the tracking markers 508. In one example, the housing 502 may be generally domed shaped with a flattened back side and the sterile cover 512 may be round. However, the housing 502 may also be pyramid shaped, cone shaped, dome shaped, dish shaped, or of any other suitable shape to meet the design criteria of a particular application. The shape of the sterile cover 512 is then designed to mate appropriately with the shape of the housing 502.

Still referring back to FIGS. 5A-5D, the housing 502 of the patient reference device 500 may be attachable to a patient reference arm. The patient reference arm may be attachable by way of the mounting bolt 510 to a Mayfield head holder or any other head securing device, such that the patient reference device is rigidly attached in a static location relative to the head securing device. In one example, the continuous edge 510 may have a seal located on the continuous edge 510 for forming a seal between the housing 502 and the sterile cover 512. In one example, the seal may be attached to the continuous edge 510 using any suitable adhesive. The sterile cover 512 may further have a sterile drape attached thereto for covering the housing 502 and a patient reference arm 500 attached to and holding the patient reference device 500 in position.

Still referring back to FIGS. 5A-5D, for example, a lens 516 of the sterile cover 512 comprises a substantially transparent plastic material that is easily sterilizable and has optical properties that are controllable, wherein infrared light that is transmitted through the lens 516 of the sterile cover 512 is reflected from the tracking markers 508 and is transmitted back through the lens 516 of sterile cover 512 without excessive diffraction which would otherwise be problematic for the tracking camera, e.g., the tracking camera 307, that is monitoring the tracking markers 508. In one example, the sterile cover 512 comprises glass, quartz, or sapphire. In some examples, the lens 516 of the sterile cover 512 may have additional optical properties, such as that of a band-pass filter that allows transmission of infrared light, but blocks any suitable portion of the frequency spectrum on each side of the IR pass band. In another example, the lens 516 of the sterile cover 512 may have the optical properties of a low-pass or a high-pass optical filter. While some examples have been given for possible optical filter characteristics, any suitable optical filter may be applied to the lens 516 for a particular application.

Still referring back to FIGS. 5A-5D, the patient reference device 500 further comprises at least one sensor (not shown) attached thereto for providing a signal to the navigation system, such as the navigation system 200, as shown in FIG. 2, which may include the control and processing unit 300, as shown in FIG. 3A. In one example, the sensor comprises an accelerometer, a force sensor, a gyroscope, a magnetometer, a strain gauge, or any other suitable sensor. The sensor may be either attached to the exterior of the housing 502 or embedded in or integrated into the housing 502. In one example, the patient reference device 500 may have a triaxial accelerometer attached thereto for sensing acceleration in any of the X, Y, and Z directions and providing the signal generated by the accelerometer to the control and processing unit 300. For example, the accelerometer mounted on the patient reference device 500 comprises one of the external I/O devices 344, as shown in FIG. 3A. The control and processing unit 300 is programmable, e.g., via one of the processing engines 370, to monitor signals from the accelerometer after the patient reference device 500 has been put into position and registered during the registrations steps, as indicated by blocks 406 and 408, as shown in FIG. 4A.

Still referring back to FIGS. 5A-5D, the control and processing system 300 is configured to receive data from the accelerometer that indicates an acceleration of the patient reference device 500 or the patient reference arm 500, e.g., by way of jolting, perhaps by one of the medical staff accidentally hitting or kicking the patient reference device 500 or the patient reference arm 500. When the acceleration, indicated by the accelerometer, exceeds a threshold such that enough force was generated that could have thrown the patient reference device from its proper fixed position, the control and processing system 300 responds accordingly. For example, the control and processing system 300 transmits data to a display device 311 which displays a warning to the operator, prompting checking the position of the patient reference device 500. In another example, the control and processing system 300 may simply require the operator of the system 200 to reregister the patient reference device 500 for ensuring that the position of the patient reference device 500 relative to the head holding device is properly perceived by the navigation system 200.

Figure 6:
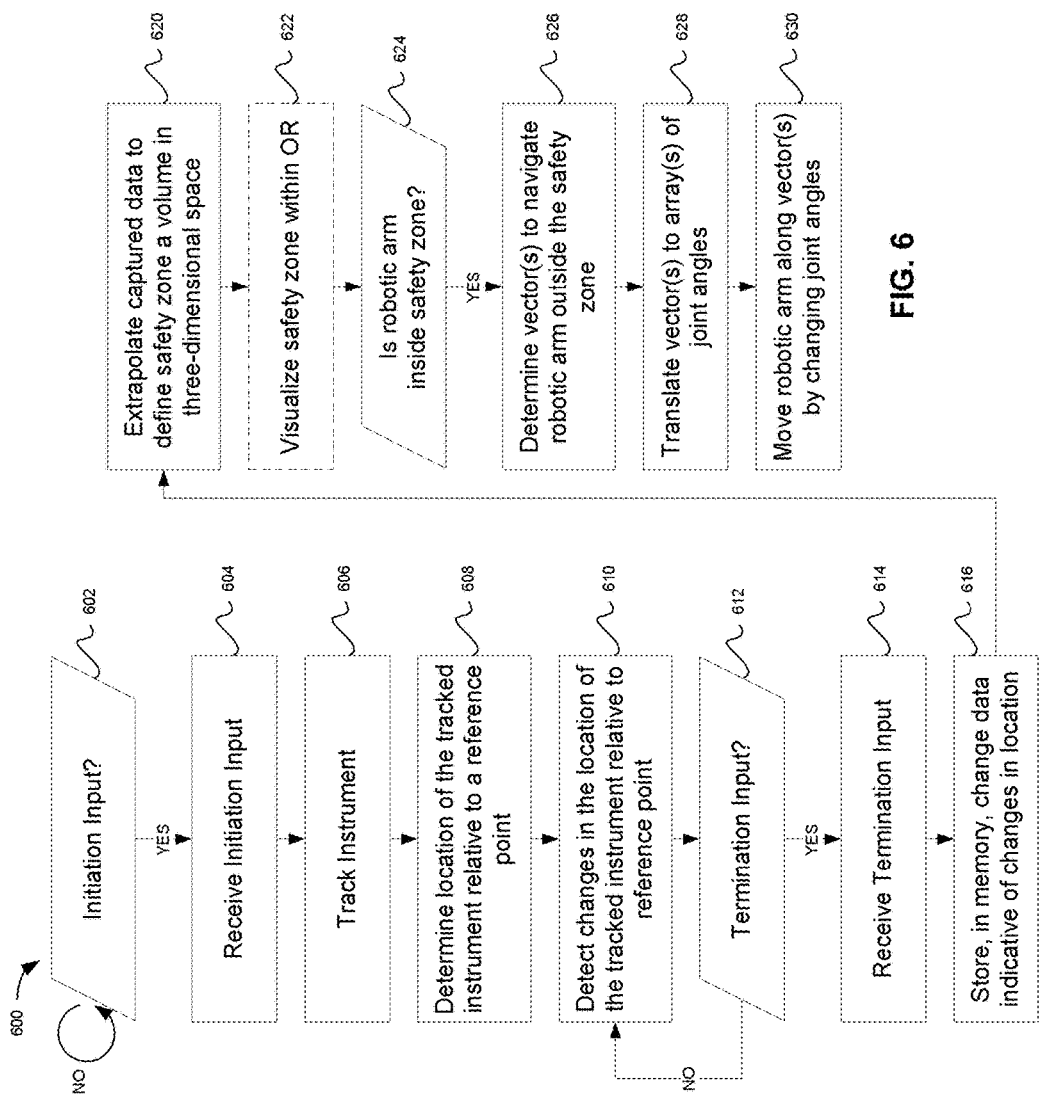
FIG. 6 is a flow chart illustrating a method of identifying a safety zone, in accordance with an embodiment of the present disclosure.

Reference is now made to FIG. 6 which illustrates a flowchart of an example method 600 for identifying a safety zone relative to a reference point. Method 600 may be implemented fully or partially by navigation system 200 and control and processing system 300 (FIG. 3A). Method 600 may contain additional or fewer processes than shown and/or described, and may be performed in a different order. Computer-readable code executable by the processor(s) 302 to perform method 600 may be stored in a computer-readable medium such as memory 304.

Method 600 utilizes tracking camera 307 to define the safety zone. Once a tracked instrument enters the field of view of tracking camera 307, changes in the location of the tracked instrument are detected by tracking camera 307 and processed by medical navigation system 200. Method 600 permits a user to identify a safety zone using a gesture based input created by a tracked instrument and detected by tracking camera 307.

Examples of tracked instruments that are suitable for defining the safety zone are shown in FIGS. 7A-7B. Shown in FIG. 7A is a first gesture instrument 702 having three tracking markers (711, 712, 713), and shown in FIG. 7B is a second gesture instrument 704 having four tracking markers (714, 715, 716, 717). The tracking markers may comprise passive reflective tracking spheres or active infrared (IR) markers that may be visible to a tracking camera, such as the tracking camera 307 of the navigation system 200. The tracking markers may be made of a variety of suitable materials, in a variety of shapes and sizes.

Each of gestures instruments 702, 704 has a handle 722, 724. Each handle is attached to an array of tracking markers that extends along an axis of the tracked instrument. As shown, handles 712, 724 are attached perpendicularly to tracking markers. As previously discussed, tracking camera 307 can detect and track an instrument within its field of view if the instrument has at least three tracking markers attached thereto. Accordingly, the array of tracking markers permits a user to draw broad brush like strokes using the gesture instrument in the air to define the safety zone. Method 600 will detect such strokes and extrapolate the strokes to define a volume in three-dimensional space. Once defined, control and processing system 300 will restrict robotic arm 305 from entering into the safety zone.

Further, as shown, first gesture instrument 702 has an array of tracking markers, wherein markers 711 and 712 are positioned in proximity to one another at a set distance apart from one another, and markers 712 and 713 are positioned in proximity to one another at a set distance apart from one another that is different from the distance between markers 711 and 712. This arrangement enables navigation system 200 to determine the orientation of tool 702. Similarly, as shown, second gesture instrument 704 has an array of tracking markers, wherein markers 714 and 715 are positioned in proximity to one another at a set distance apart from one another, and markers 716 and 717 are positioned in proximity to one another at a set distance apart from one another that is different from the distance between markers 714 and 715. Again, this arrangement enables navigation system 200 to determine the orientation of tool 704.

Other tracked instruments are also suitable for defining the safety zone in a manner similar to first and second gesture instruments 702, 704. For example, in an alternative embodiment, a tracked clinical instrument may have a dual function, as a surgical pointer tool and as a gesture instrument. Accordingly, example gestures instruments 702, 704 are non-limiting.

Because tracking camera 307 is constantly monitoring the operating room environment for tracked instruments within its field of view, an initiation input is utilized to indicate initiation of defining of the safety zone. System 300 monitors external I/O devices 333 for an initiation input continuously, as shown by block 602. Once an initiation input is detected at 602, method 600 proceeds to receive the initiation input at 604. An initiation input may be received at system 300 from a foot pedal (e.g. the press or depress of foot pedal 950 of FIG. 9A), a microphone (voice command), a mouse, a button, a keyboard, or a sensor. In one embodiment, gestures instruments 702, 704 include one or more buttons to allow for a user to initiate defining of the safety zone by pressing or depressing a button. Gestures instruments 702, 704 may communicate with system 300 via a wireless communication system. In one embodiment, medical navigation system 200 is configured to detect a specific movement of gestures instruments 702, 704 as a gesture-based initiation input.

In response to receiving the initiation input, medical navigation system 200 tracks the gesture instrument at 606 and determines the location of the tracked gesture instrument related to a reference point at 608. At 610, medical navigation system 200 detects changes in the location of the tracked gesture instrument relative to a reference point. The reference point may be of the location of the patient reference device 500 that is fixed relative to the patient's skill, or, alternatively, the location of any tracked instrument (e.g. a clinical instrument). Accordingly, the safety zone may be defined relative to the position of the patient in the OR, or alternatively, the position of a tracked clinical instrument in the OR. The initiation input may identify the chosen reference point; for example, electing between the patient reference frame and any tracked instrument within the system. By defining a safety zone relative to the patient reference frame, the user is able to provide surgeon 201 working room around the patient and prevents robotic arm 305 from interfering with the patient. On the other hand, by defining a safety zone relative to tracked instrument, the user creates a safety zone around the instrument; thereby ensuring that the robotic arm will not interfere with the instrument even if it is not in proximity to the patient.

Medical navigation system 200 continues to detect changes in the location of the tracked gestured instrument until a termination input is detected. System 300 monitors for a termination input continuously, as shown by block 612. Once a termination input is detected at 612, method 600 proceeds to receive the termination input at 612. A termination input may be received at system 300 from a foot pedal, a button, a microphone (voice command), a mouse, a keyboard, or a sensor. In one embodiment, gestures instruments 702, 704 include one or more buttons to allow for a user to terminate defining of the safety zone by pressing a button. In one embodiment, medical navigation system 200 is configured to detect a specific movement of gestures instruments 702, 704 as a gesture-based termination input (i.e. a termination gesture).

Once the defining the safety zone is terminated, system 300 stores in memory 304 change data indicative of changes in location of the tracked gesture instrument at 616. The change data identifies the safety zone relative to the reference point.

In one embodiment, medical navigation system 200 initiates a timer in response to receiving the initiation input. Medical navigation system 200 may thus also store timing information associated with the location data. For example, at t=0s, the location of the tracked gesture instrument is at coordinate (0,0,0), but at t=1s, the location of the tracked gesture instrument is at coordinate (1,1,1), and so forth.

In some embodiments, system 300 may include soft and hard termination inputs. A soft termination input indicates the termination of defining of a first safety zone and the initiation of defining a second safety zone. On the other hand, a hard termination input indicates the termination of defining safety zones generally. The soft termination input may be useful in allowing a user to define multiple safety zones.

Figure 8B:
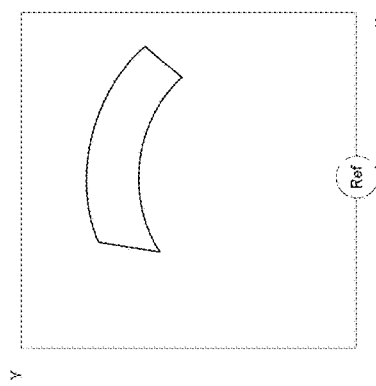
FIGS. 8A-8D illustrate exemplary two-dimensional charts of an gesture inputs and a safety zone, in accordance with an embodiment of the present disclosure.
Figure 8D:
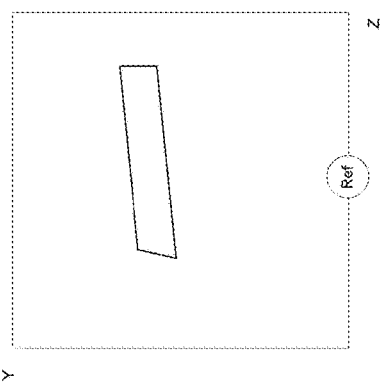

Two examples of change data indicative of a gesture input by gesture instrument 702 are shown in FIGS. 8A-8D. For simplicity the figures illustrate the gesture input using a two-dimensional grid; however, medical navigation system 200 typically detects changes in movement across three-dimensions, and the gesture input is typically three-dimensional. In addition, a time-dimension may be stored with each position coordinate. As shown, three 'lines' are detected. Each line corresponds with one of the three tracking markers 714 attached to gesture input 702. The reference point shown corresponds to the patient reference point at the patient's head (e.g. as shown in FIG. 9A).

Figure 8A:
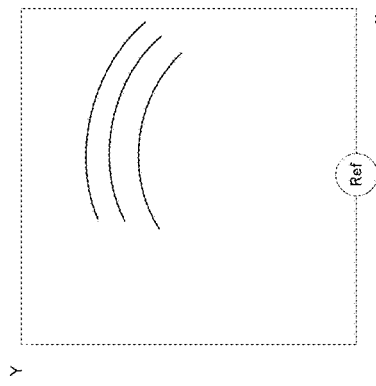
Figure 9A:
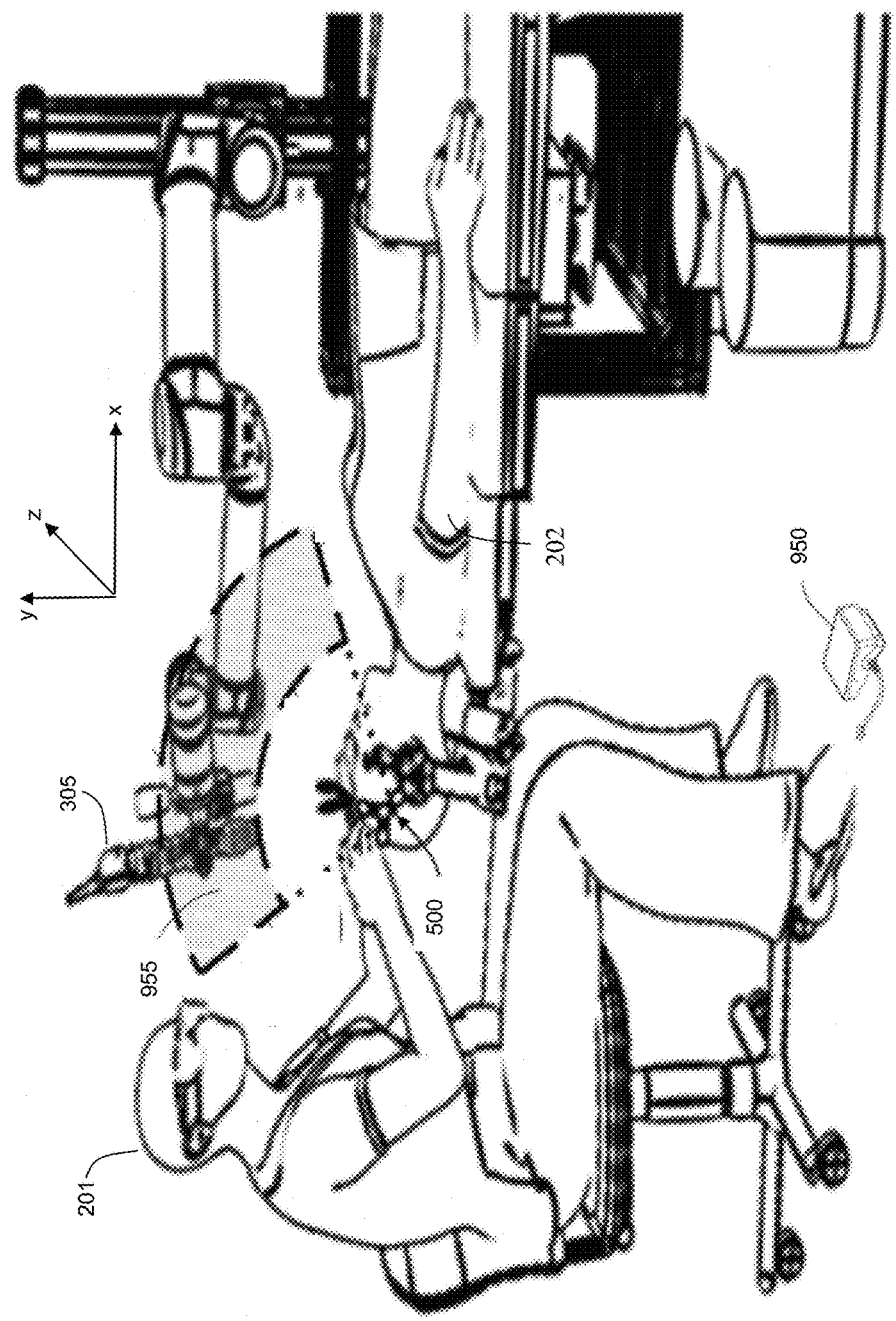
FIGS. 9A-9B illustrates a perspective view of safety zone defined in an operating room, in accordance with an embodiment of the present disclosure.

As shown in FIG. 8A, the detected gesture input represents the movement of gesture instrument 702 across the x-axis with a slight upwards arc along the y-axis. Medical navigation system 200 detects three discrete paths associated with movement of gesture instrument 702, each discrete path being associated with one of the three tracking markers 714. The gesture input is detected relative to the reference point, and the gesture input moves from the left to the right of the reference point along the x-axis (or vice-versa). An example of a safety zone in an operating room setting based on the gesture input of FIG. 8A is shown as safety zone 955 in FIG. 9A. Safety zone 955 provides surgeon 201 with room to maneuver above patient 202's head.

Figure 8C:
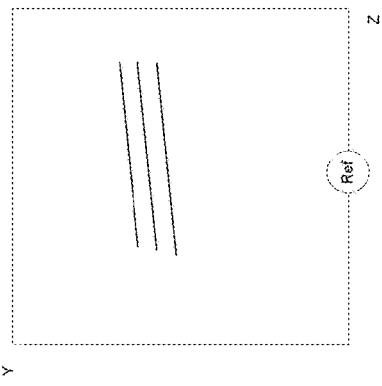

As shown in FIG. 8C, the detected gesture input represents the movement of gesture instrument 702 across the z-axis and along the y-axis. The gesture input is detected relative to the reference point, and the gesture input moves from the left to the right of the reference point along the z-axis (or vice-versa). With reference to FIG. 9A, the region along the z-axis represents patient 202's width and the region along the x-axis represents patient 202's length.

System 300 may then process stored change data (e.g. gesture inputs of FIGS. 8A and 8B) at 620 by extrapolating the stored change data based on the detected discrete paths to define a volume in three-dimensional space relative to the reference point. In one embodiment, to extrapolate the gesture input, system 300 may identify the maximum and minimum coordinates of the gesture input relative to the reference point for each of the x-, y-, and z-axes. The maximum and minimum coordinates of each axis identified in the extrapolation step may be used to define the safety zone which the robotic arm 305 is not permitted. However, such processing would result in creating a safety zone that is larger than the gesture input; as the processing smooths out cures in the gesture input. Examples of extrapolating the stored change data (gesture input) are shown in FIGS. 8B and 8D.

In FIG. 8B, the gesture input of FIG. 8A is extrapolated to define an arc-shaped area: the three discrete paths of FIG. 8A are transformed into an area representing an arc. This is shown in an operating room environment in FIG. 9A as safety zone 955. While the area shown in FIG. 8B has no depth defined along the z-axis, system 300 may extrapolate the safety zone to include every point along the z-axis; i.e. the robotic arm 305 will not be permitted along the arc-shaped region above the patient's head along the entire z-axis.

In FIG. 8D, the gesture input of FIG. 8C is extrapolated to define a trapezoid-shaped area: the three discrete paths of FIG. 8C are transformed into an area representing a trapezoid. While the area shown in FIG. 8C has no depth defined along the x-axis, system 300 may extrapolate the safety zone to include every point along the x-axis; i.e. the robotic arm 305 will not be permitted along the trapezoid-shaped region above the patient's body along the entire x-axis.

Furthermore, if gesture inputs of FIG. 8A and FIG. 8C are simultaneously defined, system 300 may interpret the gesture inputs in relation to one another. Accordingly, while gesture input of FIG. 8A has no depth information along the z-axis, and while gesture input of FIG. 8C has no depth information along the x-axis, the combination of the two gesture inputs results in a safety zone limited to the arc-shaped area above the patient's head.

Accordingly, in some embodiments, two gesture inputs are used to define a three-dimensional volume. In some embodiments, a user may explicitly indicate that the two gesture inputs represent a single three-dimensional volume, while in other embodiments, system 300 determines so automatically. System 300 may determine that the two gesture inputs represent a single three-dimensional volume based on the relationship of the two gesture inputs to one another. For example, if a first gesture input lacks depth information along a first axis, and a second gesture input lacks depth information along a second axis (as shown in FIGS. 8A-8D), then the two gesture inputs are likely to complement one another. Furthermore, if the two gesture inputs are received simultaneously one after another, then the two gesture inputs are likely to complement one another.

In some embodiments, a single gesture input received defines a three-dimensional volume. System 300 may accordingly interpret the gesture input as a volume with the operating room by extrapolating along three-dimensions at 620. Furthermore, at 620, system 300 may extrapolate gesture input to define a smooth three-dimensional volume (e.g. a spherical shape, a cube, a trapezoid, and so forth). In some embodiments, a user may guide system 300's extrapolation by selecting a shape from a list of shapes. This may be particularly helpful to define odd shapes such as a doughnut, or other shape that has a void in the middle thereof.

In some embodiments, a gesture input may define an area or volume around an obstacle. For example, the user may wish to define a safety zone in the current position of the robotic arm. Accordingly, system 300 may process the gesture input to include the area inside the circle or the volume inside the sphere.

In some embodiments, the stored change data is processed to identify a convex hull (also known as a convex envelope), which allows system 300 to identify the smallest convex polygon that surrounds the three-dimensional space identified by the gesture input. In another embodiment, the stored change data is processed to identify an alpha shape associated with the stored change data, which allows system 300 to identify linear simple curves associated with the stored change data. In yet another embodiment, system 300 may compute a bounding box surrounding the volume represented by the stored change data. Further, in some embodiments, system 300 may estimate an ellipsoid surrounding said bounding box.

At block 622, system 300 may optionally visualize the safety zone within the operating room environment. System 300 may display an image on display 311 showing the spatial position of the safety zone within the OR relative to the reference point. In some embodiments, system 300 may utilize a virtual reality headset to visualize the safety zone, or alternatively, a mixed reality system. Visualization of the defined safety zone is particularly helpful for three reasons. First, the safety zone is defined relative to a reference point. Accordingly, if the reference point moves, it is helpful to provide an indication of the spatial position of the safety zone relative to the new position of the reference point. In some embodiments, when a safety zone is defined, system 300 will automatically visualize the spatial position of the safety zone if the reference point associated with the safety zone is moved. Second, since system 300 may extrapolate and process the gesture input, visualizing the spatial position safety zone allows the user to confirm the result of the extrapolation and processing of the gesture input. Third, a user may edit or delete a safety zone based on the visualization. For example, the user interface may allow the user to select one or more defined safety zones for editing or deletion.

After the termination input is received and the safety zone defined, system 300 may determine whether robotic arm 305 is inside the safety zone at block 624. If robotic arm 305 is inside the safety zone, system 300 will navigate the arm outside the safety zone at blocks 626-630. If robotic arm 305 is not inside the safety zone, system 300 will exit method 600.

In one embodiment, system 300 will generate an alert or prompt to notify users that robotic arm 305 is inside the safety zone prior to navigating the arm. Further, in some embodiments, a user must first issue a command permitting system 300 to navigate the arm. As such, control over the user(s) of system 300 may retain control over movement of robotic arm 305 in some embodiments. In other embodiments, movement of robotic arm 305 may be fully automated without any interruptions to the user(s) of system 300.

In some embodiments, when a safety zone is defined, system 300 runs blocks 624-630 continuously to ensure that robotic arm 305 is never inside the safety zone. Accordingly, system 300 may determine in real-time, or near real-time, that robotic arm 305 is inside the safety zone and move robotic arm 305 outside of the safety zone. Robotic arm 305 may be inside the safety zone if the reference point defining the safety zone shifts (e.g. if the patient is moved, or if a tracked instrument acting as the reference point moves).

To determine whether robotic arm 305 is inside the safety zone, system 300 may determine the spatial location and pose of arm 305 within the OR. As previously discussed, distal end 369 of end effector 347 of robotic arm 305 has tracking markers attached thereto (FIGS. 3B and 3C). Tracking camera 307 may therefore determine the spatial location of distal end 369 relative to the reference point. Accordingly, based on the spatial location of distal end 369 and the geometric shape associated with arm 305, medical navigation system 200 may determine whether robotic arm 305 is inside the safety zone.

The geometric shape associated with arm 305 may be stored in a database associated with medical navigation system 200 (the database may also include the geometric shape of tracked instruments, including tracked medical instruments and tracked gesture instruments, such as gesture instruments 702 and 704). However, unlike other tracked instruments, the geometric shape of robotic arm 305 may change based on the angle of joints 348 (FIGS. 3B and 3C). Accordingly, the geometric shape database may include a series of geometric shapes based on varying combinations of joint angles. Alternatively, system 300 may compute the geometric shape of arm 305 based on a series of joint angles using a geometric model of arm 305.

In one embodiment, to determine whether robotic arm 305 is inside the safety zone, system 300 determines the spatial location of distal end 369 using the tracking markers, determines the current pose of robotic arm 305 by identifying a series of current joint angles, and models the geometric shape of robotic arm 305 within the OR based on the spatial location of distal end 369 and the series of current joint angles. System 300 may therefore determine the volume of space within the OR occupied by robotic arm 305. System 300 then determines whether robotic arm 305 is inside the safety zone by comparing the volume of space within the OR occupied by robotic arm 305 and the volume of space within the OR defining the safety zone.

If robotic arm 305 is inside the safety zone, system 300 will navigate robotic arm 305 outside the safety zone at blocks 626-630. At block 626, system 300 may determine a vector or vectors to navigate robotic arm 305 outside the safety zone. The vector or vectors define spatial positions within the OR to guide the movement of robotic arm 305. The vector or vectors may be defined relative to the tracking markers attached to the distal end of robotic arm 305. Each vector may include x-, y-, and z-coordinates.

Figure 9B:
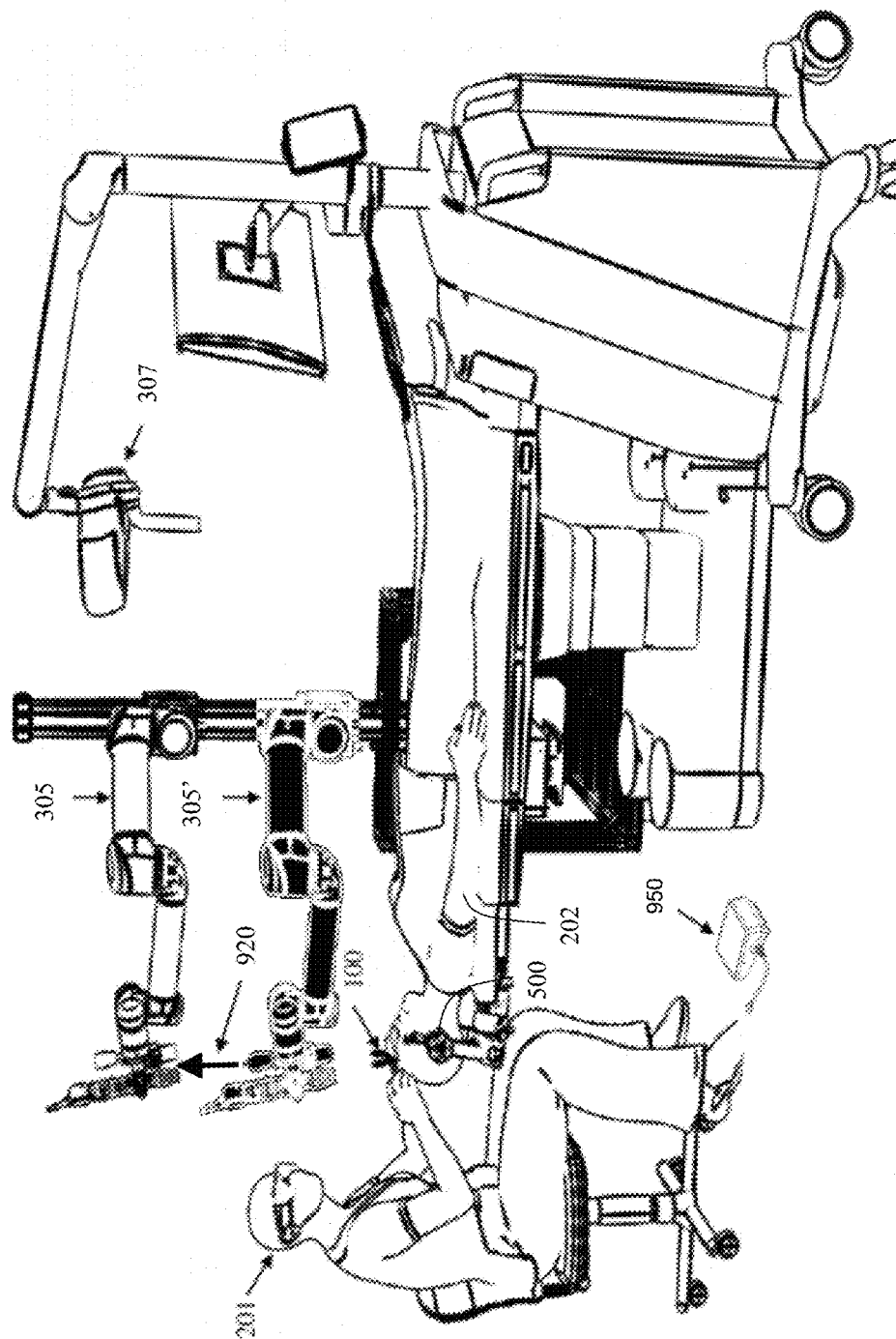

FIGS. 9A and 9B illustrate navigating robotic arm 305 outside safety zone 955. In FIG. 9A, robotic arm 305 is shown at an initial position inside safety zone 955. Reference device 500 is attached to patient 202's head, and acts as a reference point. Also attached to patient 202's head is access-port 100, through which surgeon 201 may access internal brain tissue. In FIG. 9B, robotic arm 305' is shown illustrating the initial position and robotic arm 305 is shown illustrating the final position of the arm. System 300 navigates robotic arm 305 upwards along the y-axis along vector 920 to move robotic arm 305 outside safety zone 955. In some embodiments, system 300 may visualize the vector or vectors along which robotic arm 305 will move using display 311 or virtual reality system. Additionally, system 300 may provide an audible alert prior to moving robotic arm 305.

System 300, may then translate the vector or vectors to an array of joint angles or arrays of joint angles to navigate robotic arm 305. Each spatial position within the OR (as defined by each vector) corresponds to an array of joint angles. However, movement of robotic arm 305 may require defining an array of joint angles. The joint angles indicate the angle of each joint 348 of robotic arm 305 (FIG. 3C). Additionally, if robotic arm 305 has a telescoping arm portion or lifting column (as shown in FIGS. 9A and 9B), the array of joint angles will include the length that each telescoping arm portion or lifting column is extended. In some embodiments, system 300 determines the array of joint angles needed to navigate robotic arm 305 without first determining a vector defining the spatial position of robotic arm 305.

At block 630, system 300 moves robotic arm 305 outside of the safety zone along the vector or vectors by changing the joint angles of robotic arm in accordance with the array of joint angles. Accordingly, when change data identifying the safety zone is captured, and a safety zone is defined, system 300 may move robotic arm 305 outside of the safety zone.

In one embodiment, a similar method may be used to delete previously defined safety zones. Upon receipt of a deletion input (which may be received at system 200 in a manner similar to the initiation input at 602), system 300 tracks a gesture instrument to determine the location of the tracked gesture instrument relative to a reference point. In response to receiving a termination input, system 300 stores in memory change data indicative of change location of the gesture instrument, and extrapolates captured data to define a deletion zone. System 300 then determines if a safety zone is defined inside the parameters of the deletion zone. If so, system 300 adjusts the safety zone such that the safety zone does not fall within the deletion zone. In some cases, one or more safety zones may be deleted completely. In other cases, the parameters of one of more safety zones may be altered: if the safety zone is partially inside the deletion zone, system 300 uses the boundary of the deletion zone as the boundary of the safety zone. This results in the safety zone having a reduced size.

Figure 10:
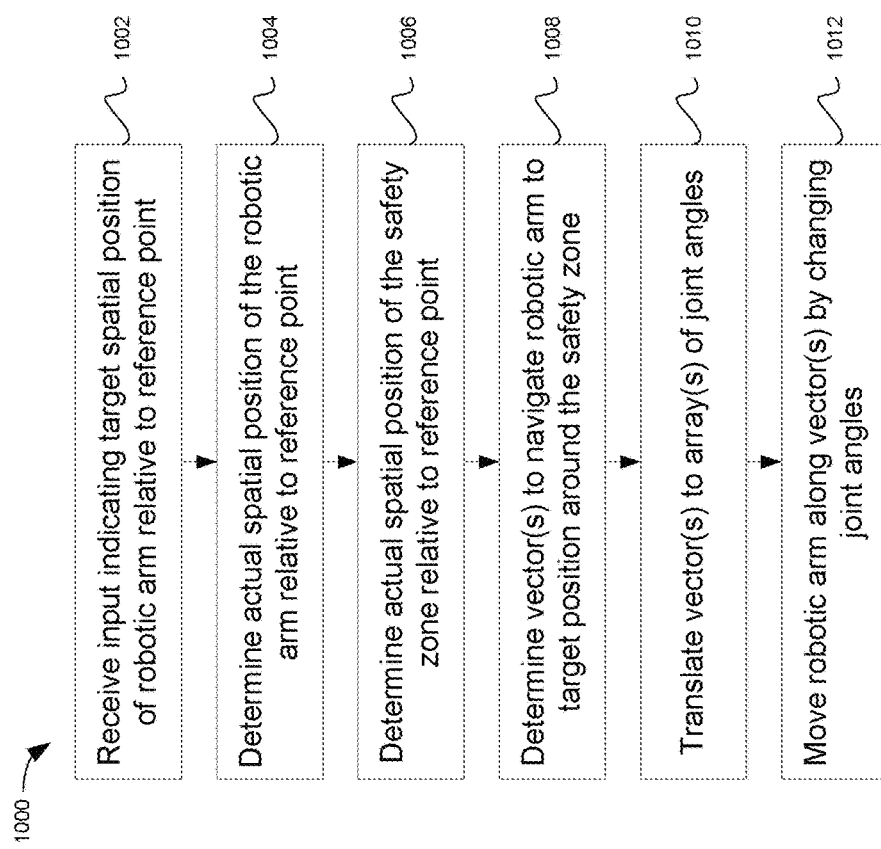
FIG. 10 is a flow chart illustrating a method of controlling the movement of a robotic arm, in accordance with an embodiment of the present disclosure.

Reference is now made to FIG. 10 which illustrates a flowchart of an example method 1000 for moving robotic arm 305 from an initial position to a final position when a safety zone is defined. Method 1000 may be implemented by fully or partially by navigation system 200 and control and processing system 300 (FIG. 3A). Method 1000 may contain additional or fewer processes than shown and/or described, and may be performed in a different order. Computer-readable code executable by the processor(s) 302 to perform method 1000 may be stored in a computer-readable medium such as memory 304.

After one or more safety zones are defined, when system 300 moves robotic arm 305, system 300 will ensure that robotic arm 305 does not enter any one of the defined safety zones by running a method in accordance with method 1000.

At block 1002, system 300 receives an input indicating a target spatial position of robotic arm 305. In one example, the input is received from an alignment system in communication with system 300. In this example, the alignment system aligns a camera attached to end effector 347 of robotic arm 305 with an access-port to enable surgeon 201 to magnify the view inside the access-port. Accordingly, in some embodiments, the target spatial position may be defined relative to a reference point, such as patient reference device 500. However, the reference point used to define the target spatial position may be different from the reference point used to define the safety zone. Accordingly, system 300 may translate the target spatial position to the same reference frame as the safety zone.

At block 1004, and in response to receiving the target spatial position, system 300 determines the actual spatial position of robotic arm 305 relative to the reference point defining the safety zone. System 300 may determine the actual spatial position of robotic arm 305 using tracking camera 307 by identifying the position of tracking markers attached to distal end 369 of robotic arm 305.

At block 1008, system 300 determines a vector or vectors to navigate robotic arm 305 to the target position around the safety zone or safety zones. Similarly to block 625, each vector may include x-, y-, and z-coordinates. As previously discussed, in determining the vector or vectors, system 300 may also determine the volume of space within the OR occupied by robotic arm 305 and the volume of space within the OR defining the safety zone.

System 300 should ideally navigate robotic arm 305 to the target position without having any part of the robotic arm breach the safety zone. However, in some cases, it may be impossible to navigate the robotic arm without breaching the safety zone. If a breach is required to reach the target position, system 300 may warn user 201 by providing an audible alert and warning sign on display 311. In such cases, system 300 may nonetheless navigate the robotic arm such as to minimize the breach of the safety zone, instead of completely avoiding a breach. Further, system 300 may visualize the safety zone, the target position of robotic arm 305, and the potential paths which robotic arm 305 may take to reach the target position.

The vector or vectors determined will depend on the actual position of robotic arm 305 at the time the input indicating the target position is received, as well as the actual position of the reference point at that time. The safety zone may shift spatially within the OR if the reference point shifts. For example, if the reference point is patient reference device 500, the safety zone will shift spatially if device 500 moves. Device 500 may move if the patient is moved. Similarly, if the reference point is a tracked instrument that is not stationary, the safety zone will shift as the tracked instrument moves about the OR.

Figure 11A:
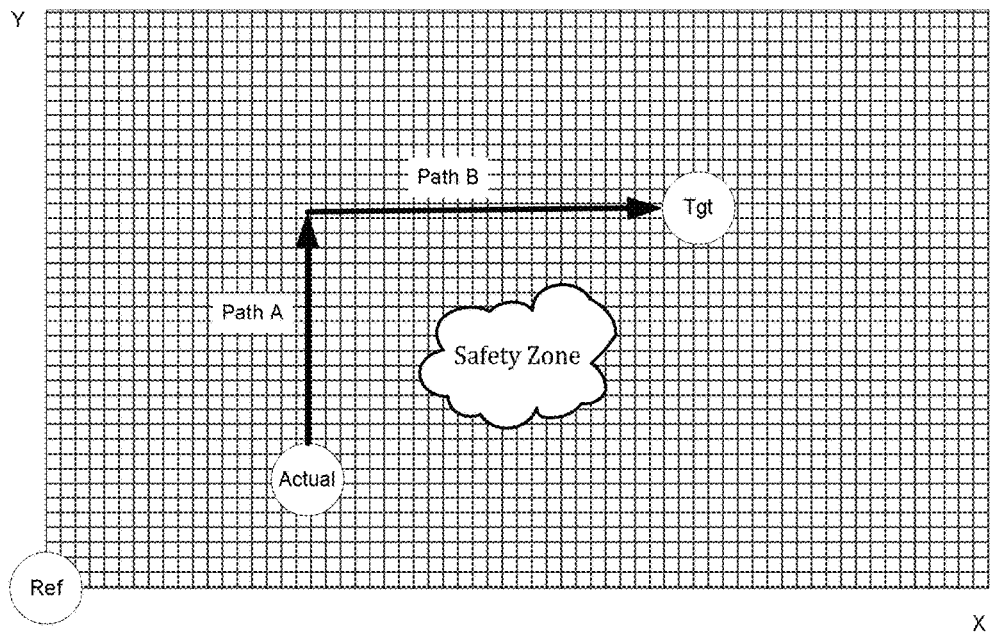
FIGS. 11A-11B illustrate exemplary two-dimensional charts of an exemplary embodiment of a safety zone and movement of a robotic arm, in accordance with an embodiment of the present disclosure.
Figure 11B:
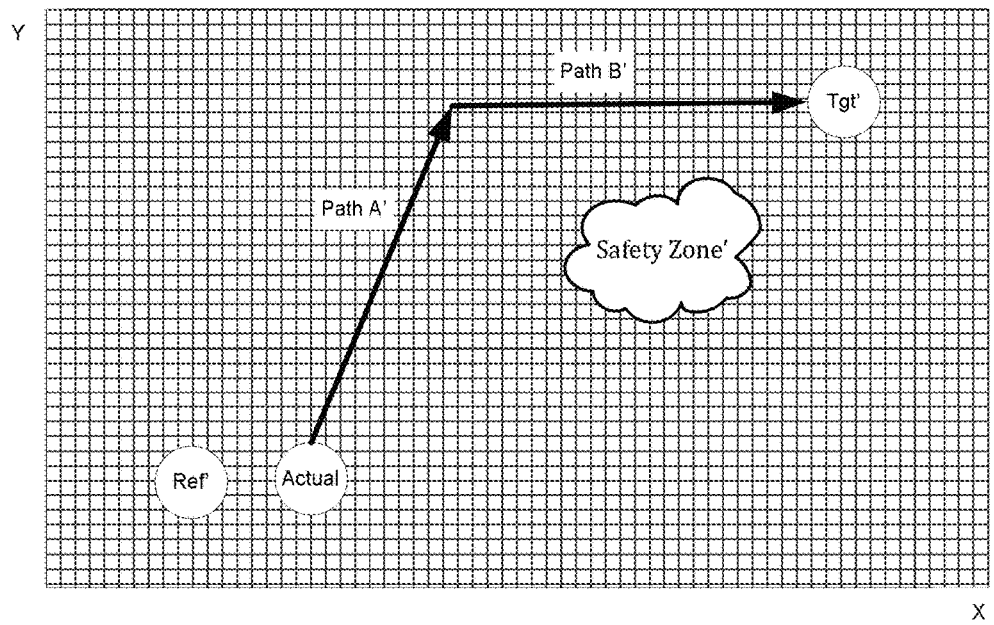

The shifting of the reference point is illustrated in FIGS. 11A and 11B. In both FIGS. 11A and 11B, the target position is provided to system 300 relative to the reference point. As shown, the reference point shifts from position Ref to position Ref between FIGS. 11A and 11B. Accordingly, while the target position provided to system 300 is the same in each instance, the actual spatial position associated with the target position is shifted from position Tgt to position Tgt'. Similarly, the actual spatial position (and volume) associated with the safety zone is shifted from position Safety Zone to position Safety Zone'. On the other hand, as shown, while the actual position of robotic arm 305 remains the same physically throughout (position Actual), the position of robotic arm 305 relative to the reference point has changed.

As shown, in FIG. 11A, robotic arm 305 may take Path A and Path B to reach position Tgt; whereas in FIG. 11B, robotic arm 305 may take Path A' and Path B' to reach Tgt'. In the example of FIG. 11B, robotic arm 305 will have to move a larger distance to reach the target position. A different set of vectors is needed to move robotic arm 305 to the target position in each figure to account for the change in the reference point.

Referring back to FIG. 10, at block 1010, system 300 translates the vector or vectors defining the path to the target position around the safety zone to an array of joint angles. At block 1012, system 300 moves robotic arm 305 along the vector or vectors by changing the joint angles of robotic arm 305. Accordingly, system 300 ensure that even though the reference position may change, the safety zone is maintained the same relative to the reference position. This allows for the safety zone to be defined relative to the patient (by using patient reference device 500 as the reference point), or relative to a tracked instrument. Furthermore, the safety zone can be defined in an intuitive manner familiar to users of the system without thinking about how the safety zone may shift as the patient or instruments move around the OR.

While method 1000 is illustrative of a single safety zone, if multiple safety zones are defined, system 300 may take into account all defined safety zones when moving robotic arm 305. When multiple safety zones are defined, each safety zone may be assigned a priority level. For example, a patient's head may be considered a high priority safety zone, whereas the position of a non-invasive clinical instrument that can be moved may be considered a low priority safety zone. Such priority level information may be stored in meta-data information associated with each safety zone. If system 300 is unable to navigate the robotic arm without breaching any of the defined safety zones, system 300 will first attempt to navigate the robotic arm by only breaching lower priority safety zones. Accordingly, system 300 will only breach high priority safety zones if system 300 is unable to navigate the robotic arm by breaching only low priority safety zones. Further, system 300 may communicate different potential paths of the robotic arm to user(s) of system 300, and prompt the user(s) to provide an additional input prior to proceeding.

The above-described embodiments are intended to be examples only. Those of skill in the art may affect alterations, modifications, and variations to the particular embodiments without departing from the scope of the application. The teachings of the present disclosure are intended to cover and embrace all suitable changes in technology.

The steps and/or operations in the flowcharts and drawings described herein are for purposes of example only. There may be many variations to these steps and/or operations without departing from the teachings of the present disclosure. For instance, the steps may be performed in a differing order, or steps may be added, deleted, or modified.

While the present disclosure is described, at least in part, in terms of methods, a person of ordinary skill in the art will understand that the present disclosure is also directed to the various components for performing at least some of the aspects and features of the described methods, be it by way of hardware components, software or any combination of the two, or in any other manner. Moreover, the present disclosure is also directed to a pre-recorded storage device or other similar computer readable medium including program instructions stored thereon for performing the methods described herein.

The present disclosure may be embodied in other specific forms without departing from the subject matter of the claims. The described example embodiments are to be considered in all respects as being only illustrative and not restrictive. The present disclosure intends to cover and embrace all suitable changes in technology. The scope of the present disclosure is, therefore, described by the appended claims rather than by the foregoing description. The scope of the claims should not be limited by the embodiments set forth in the examples, but should be given the broadest interpretation consistent with the description as a whole.

The invention claimed is:

1. A method for identifying a safety zone, using a medical navigation system, for restricting movement of a robotic arm in an operating room, the method comprising:
   receiving, at the medical navigation system, an initiation input indicating initiation of defining of the safety zone;
   in response to receiving the initiation input,
      tracking an instrument using the medical navigation system, determining a location of the tracked instrument relative to a reference point, and detecting changes in the location of the tracked instrument until a termination input is received at the medical navigation system, the termination input indicating termination of the defining of the safety zone; and storing, in memory, change data indicative of the changes in the location of the tracked instrument, the data identifying a spatial position of the safety zone relative to the reference point, wherein the safety zone is definable by at least one gesture instrument, and wherein the safety zone is spatially shiftable if the reference point shifts.

2. The method of claim 1, wherein the tracked instrument has a plurality of tracking markers attached thereto, the tracking markers forming an array extending along an axis of the tracked instrument, and wherein tracking the instrument using the medical navigation system comprises detecting a discrete path associated with each of the tracking markers as the tracked instrument moves.

3. The method of claim 2, further comprising extrapolating the change data based on the detected discrete paths to define a volume in three-dimensional space relative to the reference point.

4. The method of claim 1, wherein the reference point is a tracking marker positioned on a patient during a medical procedure, and wherein the safety zone is defined relative to the position of the patient in the operating room.

5. The method of claim 1, wherein the reference point is associated with a tracked clinical instrument, and wherein the safety zone is defined relative to the position of the tracked clinical instrument in the operating room.

6. The method of claim 4, further comprising moving the robotic arm to a target position relative to the reference point by navigating the robotic arm around the safety zone.

7. The method of claim 6, wherein the navigating the robotic arm around the safety zone comprises:

receiving an input indicating the target position of the robotic arm;

determining an actual position of the robotic arm and the safety zone relative to the reference point;

determining a vector or vectors to navigate the robotic arm to the final position around the safety zone based on the target position and the actual position of the robotic arm and the safety zone; and moving the robotic arm along the vector or vectors.

8. The method of claim 1, wherein the initiation input is any one of an initiation gesture detected by the medical navigation system, a press of a button, a voice command, and a press of foot pedal.

9. The method of claim 1, wherein the termination input is any one of a termination gesture detected by the medical navigation system, a press of a button, a voice command, and a press of foot pedal.

10. The method of claim 1, further comprising visualizing the safety zone within the operating room relative to the reference point on a display.

11. A medical navigation system comprising:
a tracking system;
a processor; and
memory, coupled to the processor and storing instructions for identifying a safety zone for restricting movement of a robotic arm in an operating room,
wherein the processor is configured to:

receive an initiation input indicating initiation of defining of the safety zone;

in response to receiving the initiation input,
track an instrument using the tracking system,
determine a location of the tracked instrument relative to a reference point, and
detect changes in the location of the tracked instrument until a termination input is received at the medical navigation system, the termination input indicating termination of the defining of the safety zone; and store, in memory, change data indicative of the changes in the location of the tracked instrument, the data identifying a spatial position of the safety zone relative to the reference point, wherein the safety zone is definable by at least one gesture instrument, and wherein the safety zone is spatially shiftable if the reference point shifts.

12. The medical navigation system of claim 11, wherein the tracked instrument has a plurality of tracking markers attached thereto, the tracking markers forming an array extending along an axis of the tracked instrument, and wherein tracking the instrument using the tracking system comprises detecting a discrete path associated with each of the tracking markers as the tracked instrument moves.

13. The medical navigation system of claim 12, wherein the processor is further configured to extrapolate the change data based on the detected discrete paths to define a volume in three-dimensional space relative to the reference point.

14. The medical navigation system of claim 11, wherein the reference point is a tracking marker positioned on a patient during a medical procedure, and wherein the safety zone is defined relative to the position of the patient in the operating room.

15. The medical navigation system of claim 11, wherein the reference point is associated with a tracked clinical instrument, and wherein the safety zone is defined relative to the position of the tracked clinical instrument in the operating room.

16. The medical navigation system of claim 14, wherein the processor is further configured to direct the robotic arm to move to a target position relative to the reference point by navigating the robotic arm around the safety zone.

17. The medical navigation system of claim 16, wherein the navigating the robotic arm around the safety zone comprises:

receiving an input indicating the target position of the robotic arm;

determining an actual positions of the robotic arm and the safety zone relative to the reference point;

determining a vector or vectors to navigate the robotic arm to the final position around the safety zone based on the target position and the actual positions of the robotic arm and the safety zone; and moving the robotic arm along the vector or vectors.

18. The medical navigation system of claim 11, wherein the initiation input is any one of an initiation gesture detected by the processor, a press of a button, a voice command, and a press of foot pedal.

19. The medical navigation system of claim 11, wherein the termination input is any one of a termination gesture detected by the processor, a press of a button, a voice command, and a press of foot pedal.

20. The medical navigation system of claim 11, wherein the processor is further configured visualize the safety zone within the operating room relative to the reference point on a display.

* * * * *